United States Patent
Choi et al.

(10) Patent No.: US 12,226,319 B2
(45) Date of Patent: Feb. 18, 2025

(54) MULTI-PORTAL SURGICAL SYSTEMS

(71) Applicant: Amplify Surgical, Inc., Laguna Hills, CA (US)

(72) Inventors: Andy Wonyong Choi, Irvine, CA (US); Dong-Hwa Heo, Seoul (KR); Jeffrey Roh, Seattle, WA (US)

(73) Assignee: Amplify Surgical, Inc., Irvine, CA (US)

( * ) Notice: Subject to any disclaimer, the term of this patent is extended or adjusted under 35 U.S.C. 154(b) by 0 days.

(21) Appl. No.: 17/902,685

(22) Filed: Sep. 2, 2022

(65) Prior Publication Data

US 2023/0104335 A1    Apr. 6, 2023

Related U.S. Application Data

(63) Continuation of application No. 16/565,403, filed on Sep. 9, 2019, now Pat. No. 11,464,648.

(51) Int. Cl.
*A61F 2/44* (2006.01)
*A61B 1/00* (2006.01)
(Continued)

(52) U.S. Cl.
CPC .......... *A61F 2/4455* (2013.01); *A61B 1/0005* (2013.01); *A61B 17/025* (2013.01); *A61B 2017/0256* (2013.01); *A61B 2017/681* (2013.01)

(58) Field of Classification Search
CPC ............ A61F 2/44–447; A61F 2/4611; A61B 17/025; A61B 2017/0256–0262; A61B 2017/3445; A61B 2017/3447
See application file for complete search history.

(56) References Cited

U.S. PATENT DOCUMENTS 3,486,505 A    12/1969  Morrison
5,171,279 A    12/1992  Mathews
(Continued)

FOREIGN PATENT DOCUMENTS

CN    105636555 A    6/2016
EP    3016617 A2    5/2016
(Continued)

OTHER PUBLICATIONS

Choi, Chang Myong et al. "How I do it? Biportal endoscopic spinal surgery (BESS) for treatment of lumbar spinal stenosis." Acta Neurochir (2016) 158:459-463; published Jan. 18, 2016.
(Continued)

*Primary Examiner* — Eduardo C Robert
*Assistant Examiner* — Steven J Cotroneo
(74) *Attorney, Agent, or Firm* — Perkins Coie LLP

(57) ABSTRACT

A multi-portal method for treating a subject's spine includes distracting adjacent vertebrae using a distraction instrument positioned at a first entrance along the subject to enlarge an intervertebral space between the adjacent vertebrae. An interbody fusion implant can be delivered into the enlarged intervertebral space. The interbody fusion implant can be positioned directly between vertebral bodies of the adjacent vertebrae while endoscopically viewing the interbody fusion implant using an endoscopic instrument. The patient's spine can be visualized using endoscopic techniques to view, for example, the spine, tissue, instruments and implants before, during, and after implantation, or the like. The visualization can help a physician throughout the surgical procedure to improve patient outcome.

16 Claims, 14 Drawing Sheets

(51) Int. Cl.
*A61B 17/02* (2006.01)
*A61B 17/68* (2006.01)

(56) References Cited

U.S. PATENT DOCUMENTS

| | | | |
|---|---|---|---|
| 5,390,683 A | 2/1995 | Pisharodi | |
| 5,437,637 A | 8/1995 | Lieber et al. | |
| 5,690,222 A | 11/1997 | Peters | |
| 5,735,290 A * | 4/1998 | Sterman | A61F 2/2427 606/8 |
| 5,762,629 A | 6/1998 | Kambin | |
| 5,782,832 A | 7/1998 | Larsen et al. | |
| 5,846,182 A | 12/1998 | Wolcott | |
| 5,888,223 A | 3/1999 | Bray | |
| 6,126,689 A | 10/2000 | Brett | |
| 6,162,170 A | 12/2000 | Foley et al. | |
| 6,348,058 B1 * | 2/2002 | Melkent | A61B 34/20 606/97 |
| 6,409,766 B1 | 6/2002 | Brett | |
| 6,641,614 B1 | 11/2003 | Wagner et al. | |
| 6,723,126 B1 | 4/2004 | Berry | |
| 6,969,392 B2 | 11/2005 | Gitis et al. | |
| 7,083,650 B2 | 8/2006 | Moskowitz et al. | |
| 7,087,055 B2 | 8/2006 | Lim et al. | |
| 7,731,751 B2 | 6/2010 | Butler et al. | |
| 7,922,729 B2 | 4/2011 | Michelson | |
| RE42,525 E | 7/2011 | Simonson | |
| 8,016,767 B2 | 9/2011 | Miles et al. | |
| 8,062,375 B2 | 11/2011 | Glerum et al. | |
| 8,353,963 B2 | 1/2013 | Glerum | |
| 8,382,842 B2 | 2/2013 | Greenhalgh et al. | |
| 8,394,145 B2 | 3/2013 | Weiman | |
| 8,398,713 B2 | 3/2013 | Weiman | |
| 8,425,613 B2 | 4/2013 | Theofilos | |
| 8,435,298 B2 | 5/2013 | Weiman | |
| 8,491,659 B2 | 7/2013 | Weiman | |
| 8,512,407 B2 | 8/2013 | Butler et al. | |
| 8,518,120 B2 | 8/2013 | Glerum et al. | |
| 8,556,979 B2 | 10/2013 | Weiman et al. | |
| 8,568,317 B1 | 10/2013 | Gharib et al. | |
| 8,632,594 B2 | 1/2014 | Williams et al. | |
| 8,632,595 B2 | 1/2014 | Weiman | |
| 8,679,183 B2 | 3/2014 | Glerum et al. | |
| 8,685,098 B2 | 4/2014 | Glerum et al. | |
| 8,709,086 B2 | 4/2014 | Glerum | |
| 8,845,731 B2 | 9/2014 | Weiman | |
| 8,845,732 B2 | 9/2014 | Weiman | |
| 8,845,734 B2 | 9/2014 | Weiman | |
| 8,852,279 B2 | 10/2014 | Weiman | |
| 8,864,833 B2 | 10/2014 | Glerum et al. | |
| 8,888,853 B2 | 11/2014 | Glerum et al. | |
| 8,888,854 B2 | 11/2014 | Glerum et al. | |
| 8,926,704 B2 | 1/2015 | Glerum et al. | |
| 8,940,048 B2 | 1/2015 | Butler et al. | |
| 8,986,386 B2 | 3/2015 | Oglaza et al. | |
| 9,034,041 B2 | 5/2015 | Wolters et al. | |
| 9,039,771 B2 | 5/2015 | Glerum et al. | |
| 9,044,342 B2 | 6/2015 | Perloff et al. | |
| 9,078,769 B2 | 7/2015 | Farin | |
| 9,119,730 B2 | 9/2015 | Glerum et al. | |
| 9,125,757 B2 | 9/2015 | Weiman | |
| 9,149,367 B2 | 10/2015 | Davenport et al. | |
| 9,155,628 B2 | 10/2015 | Glerum et al. | |
| 9,186,258 B2 | 11/2015 | Davenport et al. | |
| 9,198,765 B1 | 12/2015 | Pimenta | |
| 9,198,772 B2 | 12/2015 | Weiman | |
| 9,204,972 B2 | 12/2015 | Weiman et al. | |
| 9,204,974 B2 | 12/2015 | Glerum et al. | |
| 9,211,196 B2 | 12/2015 | Glerum et al. | |
| 9,216,095 B2 | 12/2015 | Glerum et al. | |
| 9,226,836 B2 | 1/2016 | Glerum | |
| 9,271,843 B2 | 3/2016 | Fabian et al. | |
| 9,278,008 B2 | 3/2016 | Perloff et al. | |
| 9,283,092 B2 | 3/2016 | Siegal et al. | |
| 9,295,562 B2 | 3/2016 | Lechmann et al. | |
| 9,308,099 B2 | 4/2016 | Triplett et al. | |
| 9,320,613 B2 | 4/2016 | Dmuschewsky | |
| 9,351,848 B2 | 5/2016 | Glerum et al. | |
| 9,358,126 B2 | 6/2016 | Glerum et al. | |
| 9,358,128 B2 | 6/2016 | Glerum et al. | |
| 9,358,129 B2 | 6/2016 | Weiman | |
| 9,370,434 B2 | 6/2016 | Weiman | |
| 9,402,739 B2 | 8/2016 | Weiman et al. | |
| 9,408,708 B2 | 8/2016 | Greenhalgh | |
| 9,414,934 B2 | 8/2016 | Cain | |
| 9,414,936 B2 | 8/2016 | Miller et al. | |
| 9,452,063 B2 | 9/2016 | Glerum et al. | |
| 9,456,903 B2 | 10/2016 | Glerum et al. | |
| 9,474,623 B2 | 10/2016 | Cain | |
| 9,474,625 B2 | 10/2016 | Weiman | |
| 9,480,573 B2 | 11/2016 | Perloff et al. | |
| 9,480,578 B2 | 11/2016 | Pinto | |
| 9,486,325 B2 | 11/2016 | Davenport et al. | |
| 9,486,328 B2 | 11/2016 | Jimenez et al. | |
| 9,492,283 B2 | 11/2016 | Glerum | |
| 9,492,287 B2 | 11/2016 | Glerum et al. | |
| 9,492,288 B2 | 11/2016 | Wagner et al. | |
| 9,510,954 B2 | 12/2016 | Glerum et al. | |
| 9,522,068 B2 | 12/2016 | Goel et al. | |
| 9,539,108 B2 | 1/2017 | Glerum et al. | |
| 9,545,319 B2 | 1/2017 | Farin | |
| 9,554,918 B2 | 1/2017 | Weiman | |
| 9,561,116 B2 | 2/2017 | Weiman et al. | |
| 9,561,117 B2 | 2/2017 | Lechmann et al. | |
| 9,566,168 B2 | 2/2017 | Glerum et al. | |
| 9,579,124 B2 | 2/2017 | Gordon et al. | |
| 9,579,130 B2 | 2/2017 | Oglaza et al. | |
| 9,597,197 B2 | 3/2017 | Lechmann et al. | |
| 9,597,200 B2 | 3/2017 | Glerum et al. | |
| 9,610,175 B2 | 4/2017 | Barreiro et al. | |
| 9,610,176 B1 | 4/2017 | Abdou | |
| 9,615,937 B2 | 4/2017 | Barreiro | |
| 9,655,744 B1 | 5/2017 | Pimenta | |
| 9,888,859 B1 | 2/2018 | Spangler et al. | |
| 9,901,457 B2 * | 2/2018 | Sack | A61F 2/4425 |
| 10,105,238 B2 | 10/2018 | Koch et al. | |
| 10,201,431 B2 | 2/2019 | Slater et al. | |
| 10,327,912 B1 * | 6/2019 | Suddaby | A61F 2/442 |
| 10,945,859 B2 | 3/2021 | Ewer et al. | |
| 11,464,648 B2 | 10/2022 | Choi et al. | |
| 2001/0005796 A1 * | 6/2001 | Zdeblick | A61B 17/282 623/17.11 |
| 2002/0107573 A1 | 8/2002 | Steinberg | |
| 2002/0143401 A1 | 10/2002 | Michelson | |
| 2003/0028251 A1 * | 2/2003 | Mathews | A61M 25/10 623/23.62 |
| 2003/0060687 A1 | 3/2003 | Kleeman et al. | |
| 2003/0216748 A1 | 11/2003 | Gitis et al. | |
| 2003/0236472 A1 | 12/2003 | Van Hoeck et al. | |
| 2006/0149279 A1 | 7/2006 | Mathews | |
| 2007/0005088 A1 | 1/2007 | Lehuec et al. | |
| 2007/0276406 A1 | 11/2007 | Mahoney et al. | |
| 2009/0281551 A1 | 11/2009 | Frey | |
| 2010/0331883 A1 | 12/2010 | Schmitz et al. | |
| 2011/0184422 A1 | 7/2011 | Mathews | |
| 2013/0103103 A1 | 4/2013 | Mire et al. | |
| 2014/0121774 A1 * | 5/2014 | Glerum | A61F 2/447 623/17.16 |
| 2014/0249631 A1 | 9/2014 | Weiman | |
| 2014/0277497 A1 | 9/2014 | Bennett et al. | |
| 2014/0303730 A1 * | 10/2014 | McGuire | A61B 17/8841 623/17.12 |
| 2014/0324044 A1 | 10/2014 | Haufe et al. | |
| 2015/0066145 A1 | 3/2015 | Rogers et al. | |
| 2015/0265320 A1 | 9/2015 | Hynes et al. | |
| 2015/0342586 A1 | 12/2015 | Lim et al. | |
| 2016/0051373 A1 | 2/2016 | Faulhaber | |
| 2016/0128846 A1 | 5/2016 | Voellmicke | |
| 2016/0199194 A1 * | 7/2016 | Slater | A61F 2/447 623/17.16 |
| 2016/0270772 A1 | 9/2016 | Beale et al. | |
| 2016/0278791 A1 | 9/2016 | Pellegrino et al. | |
| 2016/0310291 A1 | 10/2016 | Greenhalgh | |
| 2017/0042695 A1 | 2/2017 | Foley et al. | |

(56) References Cited

U.S. PATENT DOCUMENTS

| | | |
|---|---|---|
| 2017/0056200 A1 | 3/2017 | Koch et al. |
| 2017/0065269 A1* | 3/2017 | Thommen .......... A61B 1/00154 |
| 2017/0105845 A1 | 4/2017 | Glerum et al. |
| 2018/0310975 A1 | 11/2018 | Haufe et al. |
| 2019/0142407 A1* | 5/2019 | Jung ...................... A61B 18/14 600/104 |
| 2019/0142408 A1* | 5/2019 | Jung ...................... A61F 2/4644 600/104 |
| 2019/0209154 A1 | 7/2019 | Richter et al. |
| 2020/0015925 A1 | 1/2020 | Scheib |
| 2020/0107824 A1 | 4/2020 | Fleischer |
| 2020/0383675 A1* | 12/2020 | Jung ................. A61B 17/3496 |
| 2021/0068863 A1 | 3/2021 | Choi et al. |
| 2022/0175418 A1 | 6/2022 | Ebersole et al. |

FOREIGN PATENT DOCUMENTS

| | | |
|---|---|---|
| EP | 3038565 A1 | 7/2016 |
| JP | 6096282 B2 | 2/2017 |
| WO | 2013052807 A2 | 4/2013 |
| WO | 2013109346 A1 | 7/2013 |
| WO | 2013173767 A1 | 11/2013 |
| WO | 2014151162 A1 | 9/2014 |
| WO | 2014164625 A1 | 10/2014 |
| WO | 2017015165 A1 | 1/2017 |
| WO | 2017027277 A1 | 2/2017 |
| WO | 2017035155 A1 | 3/2017 |
| WO | 2017051416 A1 | 3/2017 |
| WO | 2021050577 A1 | 3/2021 |

OTHER PUBLICATIONS

Eum, Jin Hwa et al. "Percutaneous biportal endoscopic decompression for lumbar spinal stenosis: a technical note and preliminary clinical results." J Neurosurg Spine 24:602-607, Apr. 2016; published online Jan. 1, 2016.

Innovasive Inc. "Innovasive DualX LLIP expanding IBFD Product Information and Instructions for Use." May 2018, 2 pages.

International Bureau, Written Opinion, PCT Patent Application PCT/US2016/048222 filed Aug. 23, 2016; mailed Mar. 2, 2017, 4 pages.

ISA, International Search Report and Written Opinion, PCT Patent Application PCT/US2020/049982, mailed Jan. 26, 2021, 21 pages.

Kim, Jin-Sung et al., "Endoscope-assisted oblique lumbar interbody fusion for the treatment of cauda equina syndrome: a technical note." Eur Spine J (2017) 26:397-403.

Japanese Office Action for Application No. 2022-541192 mailed Mar. 11, 2024, 4 pages.

European Search Report for Application No. 20863847.8 mailed Sep. 13, 2023, 7 pages.

* cited by examiner

MULTI-PORTAL SURGICAL SYSTEMS

CROSS-REFERENCE TO RELATED APPLICATION

The present application is a continuation of U.S. patent application Ser. No. 16/565,403, filed Sep. 9, 2019 (now U.S. Pat. No. 11,464,648), and entitled "MULTI-PORTAL SURGICAL SYSTEMS," which is incorporated by reference in its entirety.

TECHNICAL FIELD

The present disclosure relates generally to medical systems and, more particularly, to systems, devices, and methods for performing multi-portal surgical procedures.

BACKGROUND

Individuals often suffer from damaged or displaced spinal discs and/or vertebral bodies due to trauma, disease, degenerative defects, or wear over an extended period of time. One result of this displacement or damage to a spinal disc or vertebral body may be chronic back pain. A common procedure for treating damage or disease of the spinal disc or vertebral body may involve partial or complete removal of an intervertebral disc. An implant (commonly referred to as an interbody spacer) can be inserted into the cavity created where the intervertebral disc was removed to help maintain height of the spine and/or restore stability to the spine. An interbody spacer may also provide a lordotic correction to the curvature of the spine. An example of an interbody spacer that has been commonly used is a fixed dimension cage, which typically is packed with bone and/or bone-growth-inducing materials. Unfortunately, it may be difficult to implant the interbody spacer at the intended implantation site between vertebral bodies. Additionally, conventional surgical techniques can cause a significant amount of trauma at or near the implantation site, which can significantly increase recovery time and lead to patient discomfort. Accordingly, there is a need for improved surgical systems, visualization techniques, and/or related technologies.

DETAILED DESCRIPTION

Figure 1:
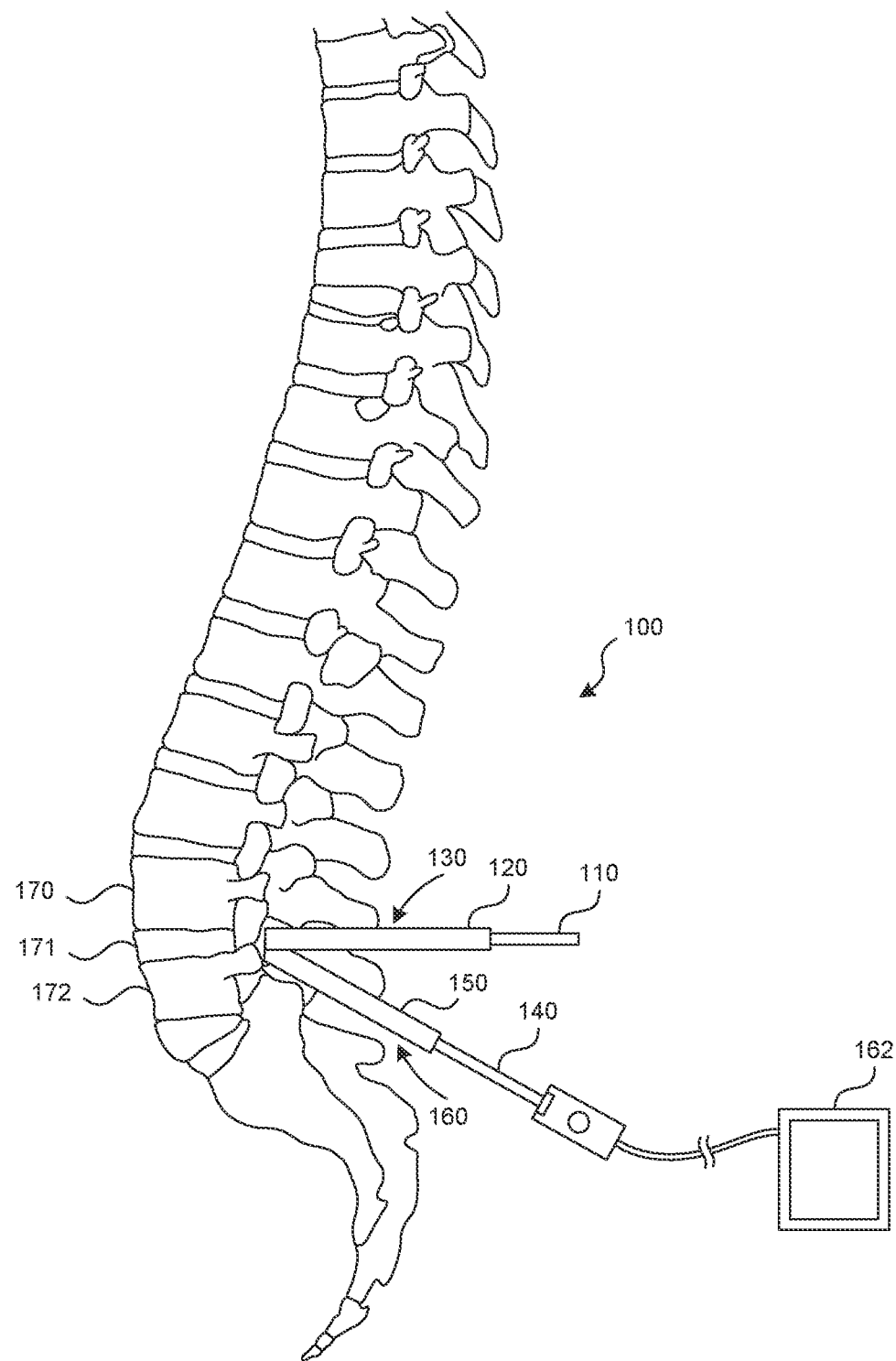
FIG. 1 is a side view of a multi-portal surgical system in accordance with an embodiment of the disclosure.

The following disclosure describes various embodiments of medical systems and devices and associated methods of use. At least some embodiments of a surgical system provide visualization capability. A series of instruments can be delivered via portal sites and used to alter tissue (e.g., shape, crush, separate, cut, debulk, break, fracture, or remove tissue), prepare an implantation site, implant a device, combinations thereof, or the like. Instrument visualization can help a physician prevent or limit injury or damage to non-targeted organs and tissues. In endoscopic-assisted surgeries, devices can be precisely implanted using minimally-invasive techniques to improve outcomes and reduce recovery times. Certain details are set forth in the following description and in FIGS. 1-13 to provide a thorough understanding of such embodiments of the disclosure. Other details describing well-known structures and systems often associated with, for example, surgical procedures are not set forth in the following description to avoid unnecessarily obscuring the description of various embodiments of the disclosure.

A. Overview

At least some embodiments are directed to multi-portal surgical systems. The surgical systems can be used to treat patients with damaged or displaced spinal discs and/or vertebral bodies. The surgical systems can be used to implant a fixed or expandable interbody device to space apart vertebral bodies, restore stability of the spine, provide lordotic correction, combinations thereof, or the like. In spinal fusion procedures, interbody devices can be used alone or in combination with bone, bone-growth-inducing materials, fixation devices (e.g., pedicle screw systems, fixation rods, etc.), or the like. The patient's spine can be visualized using endoscopic techniques to view, for example, the spine (e.g., vertebral spacing, vertebral alignment, etc.), tissue (e.g., damaged or displaced sections of intervertebral cartilage disc, tissue contributing to nerve compression, etc.), instruments and implants before, during, and after implantation, or the like. The visualization can help a physician throughout the surgical procedure to improve patient outcome.

The surgical system can provide access to the surgical site. The implementation site can be prepared by performing a discectomy, interbody preparation procedure, or the like. One or more devices (e.g., implants, fusion devices, etc.) can be delivered and placed within the patient. In some embodiments, decompression procedures can be performed to minimize or reduce pressure applied to nerve tissue and can include removing tissue contributing to stenosis, tissue pushing against nerve tissue, bulging sections of intervertebral cartilage disc, or the like. For example, decompression procedures can be performed to enlarge an epidural space to reduce spinal cord compression.

One surgical method includes positioning a distraction instrument between adjacent vertebrae at a first portal site along the patient to enlarge an intervertebral space. A tissue removal device can be used to clear and prepare the enlarged intervertebral space for implantation. An interbody fusion implant can be delivered into the enlarged intervertebral space. The expanding interbody fusion implant is endoscopically viewed using an endoscopic instrument, which is positioned at a second entrance along the patient. Endoscopic viewing can be used to evaluate whether the expanded interbody fusion implant is at the desired location, assist in delivering bone graft material, or other steps that promote bone healing and facilitate spinal fusion. Other visualization techniques can be used in combination with the endoscopic viewing. For example, fluoroscopy can be used in combination with endoscopic viewing.

In some embodiments, a multi-portal endoscopy-assisted method for treating a subject includes performing at least a portion of a surgical procedure by using a first portal site. At least a portion of the surgical procedure uses an endoscope positioned via a second portal site spaced apart from the first portal site. The spacing can be selected based on location and accessibility of the treatment site(s), whether along the spine or at another location.

In some embodiments, a multi-portal method for treating a subject's spine includes distracting adjacent vertebrae using a distraction instrument positioned at a first entrance along the subject to enlarge an intervertebral space between the adjacent vertebrae. An interbody fusion implant is delivered into the enlarged intervertebral space. The interbody fusion implant is positioned directly between vertebral bodies of the adjacent vertebrae while being endoscopically viewed using an endoscopic instrument. The endoscopic instrument can be positioned at a second entrance along the subject. The positions of the first and second entrances can be selected based on the accessibility of the implantation site.

In some yet further embodiments, a multi-portal method for treating a spine of a subject includes positioning a first cannula at a first portal along the subject. A first vertebral body and a second vertebral body are distracted using one or more distraction instruments, which can extend through the first cannula. The interbody fusion implant can be moved, via the first cannula, toward an intervertebral implantation site between the distracted first and second vertebral bodies. At least a portion of the intervertebral implantation site and at least a portion of the interbody fusion implant can be visualized using an endoscopic instrument positioned at a second portal along the subject.

In some embodiments, a spinal implant delivery instrument includes an elongated body configured to be positioned in a cannula and a distractor assembly. The distractor assembly can be coupled to the elongated body and movable from a delivery state to an expanded state to distract first and second vertebral bodies. In certain embodiments, the distractor assembly in the delivery state is configured for insertion into an intervertebral space between the first and second vertebral bodies and in the expanded state is configured to hold apart distracted first and second vertebral bodies while an interbody fusion implant is delivered into the intervertebral space.

In further embodiments, a spinal implant delivery instrument includes an elongated body configured to be positioned in a cannula and a distractor assembly coupled to the elongated body. The distractor assembly is movable from a delivery state to an expanded state to distract first and second vertebral bodies. The distractor assembly in the delivery state is configured for insertion into an intervertebral space and in the expanded state is configured to hold apart the distracted first and second vertebral bodies while an interbody fusion implant is delivered. The interbody fusion implant can be delivered from the distractor assembly and into the intervertebral space. In some embodiments, a driver is detachably couplable to a rotatable connection interface of the interbody fusion implant. The driver can move axially to move the interbody fusion implant directly between the first and second vertebral bodies. The driver is configured to expand the interbody fusion implant from a collapsed configuration to a deployed configuration. The distractor assembly can include a jaw operable to define a delivery gap through which the interbody fusion implant can be delivered.

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples among other possible examples.

B. Multi-Portal Surgical Systems

FIG. 1 is a side view of a spinal surgical system 100 ("system 100") positioned along a human subject's spine in accordance with an embodiment of the disclosure. The system 100 can include an instrument assembly 130 and a visualization assembly 160. The instrument assembly 130 can be used to perform at least a portion of a surgical procedure while the visualization assembly 160 provides visualization. The instrument assembly 130 can include an instrument 110 and a cannula 120. Ports can be used to facilitate insertion of the instrument assembly 130 and/or visualization assembly 160. For example, the visualization assembly 160 can be positioned in an endoscope port, and the instrument assembly 130 can be positioned in an instrument port.

A series of instruments can be delivered through the cannula 120 to perform a surgical procedure. In some procedures, the instrument 110 can be used to prepare an implantation site by, for example, moving organs or tissue (e.g., moving nerve tissue), removing tissue (e.g., removing the intervertebral disc 171, tissue contributing to stenosis, etc.), preparing vertebral bodies (e.g., roughening or shaping vertebral endplates), or the like. The instrument 110 can be removed and a distraction instrument can be delivered through the cannula 120. The distraction instrument can distract adjacent vertebrae 170, 172, thereby enlarging the intervertebral space. An interbody fusion implant can be delivered through the cannula 120 and into the enlarged intervertebral space. In expandable embodiments, the interbody spacer or fusion implant can be expanded to contact vertebral endplates. During the procedure, the visualization assembly 160 can provide endoscopic viewing of delivery paths, organs, tissue (e.g., nerve tissue) implantation sites, interbody fusion devices (e.g., before, during, and/or after delivery), instrument(s), and other areas or features of interest. The position of the portal sites for the instrument assembly 130 and the visualization assembly 160 can be selected based on the procedure to be performed and optical characteristics (e.g., field of view, zoom capability, etc.) of the visualization assembly 160, as discussed in connection with FIG. 4.

With continued reference to FIG. 1, the visualization assembly 160 can include a visualization device 140 and a cannula 150. The cannula 150 can help a physician when switching between visualization devices. In some embodiments, the visualization assembly 160 can be used without the cannula 150. For example, the visualization device 140 in the form of a low-profile fiber optic endoscope positioned directly through an incision, an endoscopic port, or the like. The visualization device 140 can include one or more endoscopes having, without limitation, fiber optics (e.g., optical fibers), lenses, imaging devices, working lumens, light source controls, or the like for direct viewing or viewing via a display 162. In some embodiments, the visualization device 140 can include a lumen through which fluid flows to irrigate the surgical site. For example, saline, or another suitable liquid, can be pumped through the visualization device 140 to remove tissue (e.g., loose tissue, bone dust, etc.) or other material impairing visualization. The visualization device 140 can illuminate the body cavity and enable high-resolution video visualization. A light source (e.g., a laser, light-emitting diode, etc.) located near or at the proximal end of the fiber optics can be used to transmit light to the distal end and provide illuminating light. This enables a surgeon to safely navigate into the subject's body and to illuminate specific body anatomy to view vertebral spacing, vertebral structures, nerves, bony buildup (e.g., buildup that could be irritating and pressing against nerves contributing to nerve compression), etc. In some embodiments, visualization optics for vision and illumination are included within the distal tip of the visualization device 140. The configuration and functionality of the visualization device 140 can be selected based on the desired field of view, viewing resolution, pan/zoom functionality, or the like.

Figure 3:
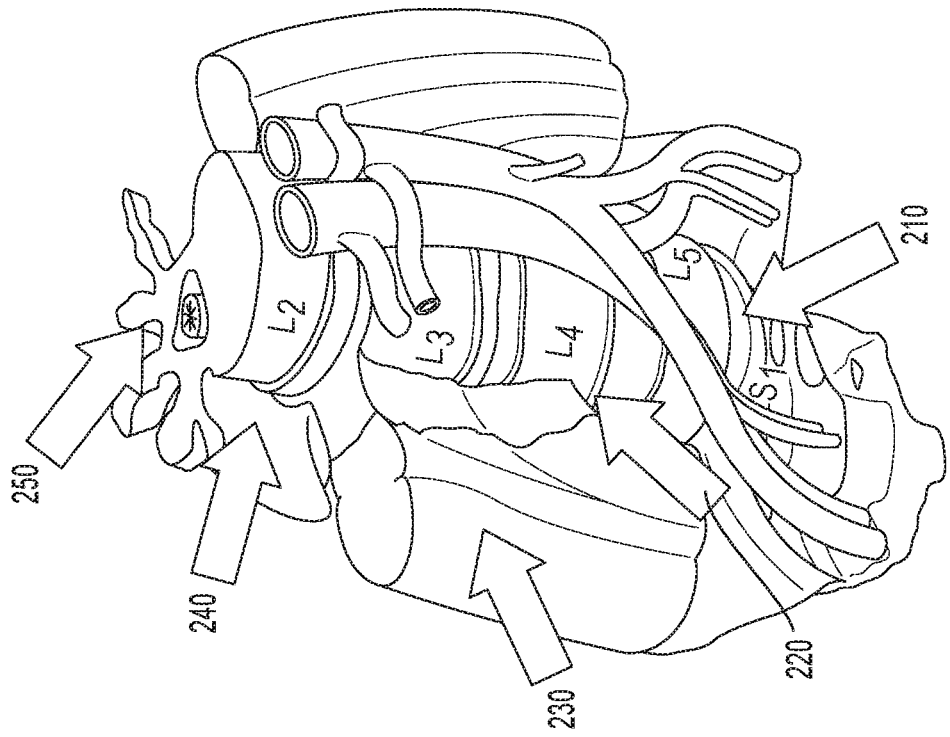
FIG. 3 is an isometric view of the lumbar spine of FIG. 2.
Figure 2:
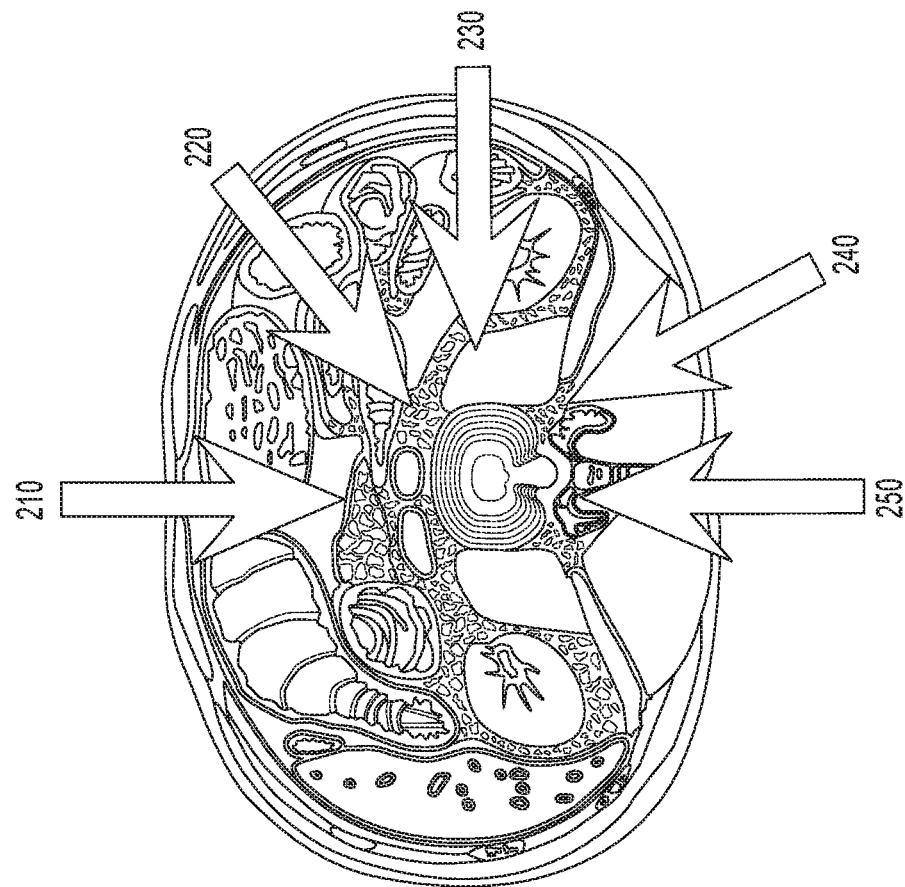
FIG. 2 is a schematic top plan view showing surgical approaches to a lumbar spine for performing interbody fusion procedures.

FIG. 2 is a schematic top plan view along the lumbar spine of a human subject and illustrates example approaches for performing interbody fusion procedures suitable for the system 100 of FIG. 1. FIG. 3 is an isometric view of the lumbar spine of FIG. 2. Referring to FIGS. 2 and 3, surgical instruments can be delivered via different paths, including an anterior lumbar interbody fusion (ALIF) path 210, an oblique lumbar interbody fusion (OLIF) path 220, a lateral or extreme lateral lumbar interbody fusion (LLIF or XLIF) path 230, a transforaminal lumbar interbody fusion (TLIF) path 240, and a posterior lumbar interbody fusion (PLIF) path 250. Example TLIF and PLIF procedures are discussed in connection with FIGS. 4-6.

With continued reference to FIGS. 2 and 3, the number and configuration of interbody fusion devices can be selected based on the fusion procedure to be performed. In one example TLIF procedure, the transforaminal path 240 may be employed to implant a single small expandable or non-expandable interbody spacer at the intervertebral space. In one example PLIF procedure, two interbody spacers can be delivered along the posterior path 250 and implanted at the intervertebral space. The two interbody spacers can cooperate to keep the vertebral bodies at the desired spacing and may be larger than the TLIF spacer. Additionally, multiple interbody spacers can provide lordotic correction by providing support at different heights. In one example LLIF procedure, a single relatively large interbody spacer can be delivered along the lateral path 230 and implanted to provide asymmetrical support. In one example ALIF procedure, an asymmetric interbody spacer can be delivered along the anterior path 210 to provide support consistent with lordosis at that portion of the spine. Lateral approaches, transforaminal approaches, and anterior approaches can be used to access the cervical spine, thoracic spine, etc. The number of instruments, configurations of instruments, implants, and surgical techniques can be selected based on the condition to be treated.

Figure 4:
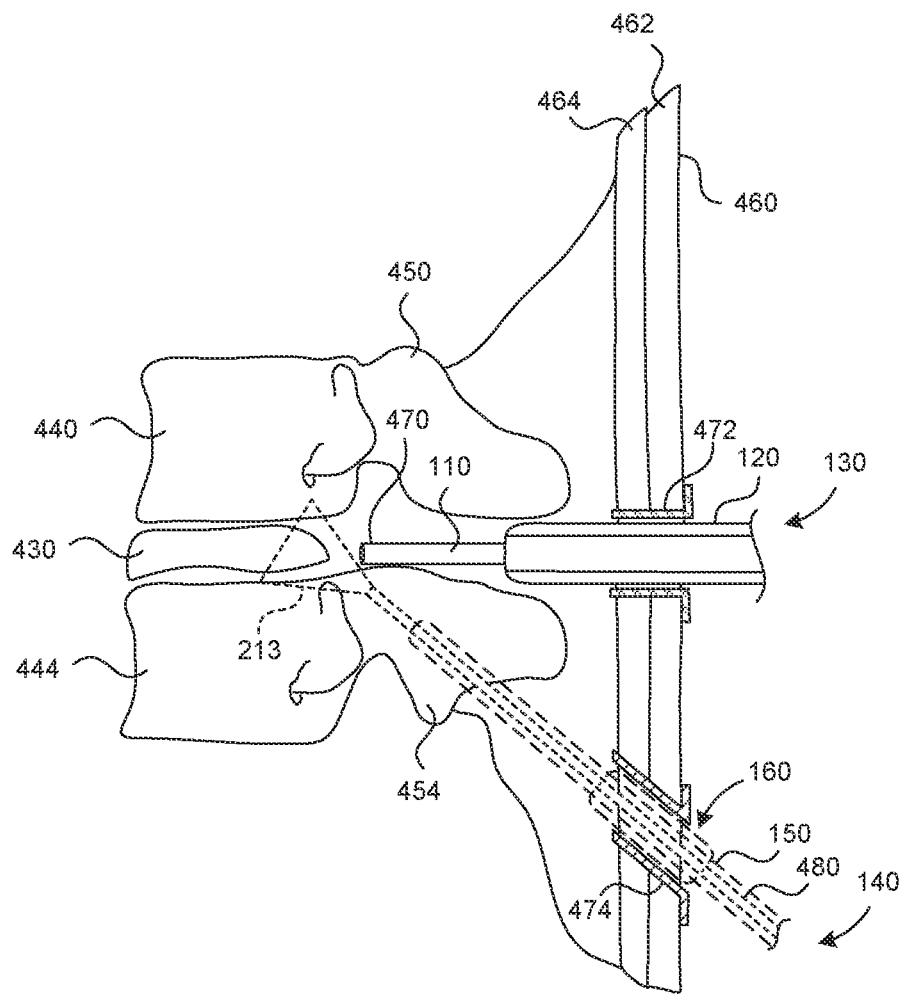
FIG. 4 is a side view of a tissue removal device positioned between adjacent vertebrae and a visualization device positioned to visualize a working area in accordance with an embodiment of the disclosure.

FIG. 4 is a detailed side view of the instrument assembly 130 positioned to perform a TLIF or PLIF procedure in accordance with embodiments of the disclosure. The instrument assembly 130 can extend through a port 472, and the visualization assembly 160 can extend through a port 474. The illustrated instrument assembly 130 can extend through the subject's skin 460, through subcutaneous tissue 462, and adjacent to or through supraspinal ligament 464. The visualization assembly 160 has a field of view 213 suitable for viewing the spinal column and can be positioned using, for example, a transforaminal approach, a posterior approach, or a lateral approach. The illustrated visualization assembly 160 is positioned to enable viewing an intervertebral disc 430 and a tissue removal tip 470 of the instrument 110, which is illustrated between spinous processes 450, 454 of vertebrae 440, 444, respectively. Fluoroscopy, MR imaging, CT imaging, direct visualization, or other visualization techniques can be used in addition to or in lieu of the endoscopic viewing.

The tissue removal tip 470 can be advanced in the anterior direction to remove the intervertebral disc 430, or other unwanted tissue, including, without limitation, tissue bulging from disc 430 (or other discs), bone (e.g., lamina, lateral recesses, facets including the inferior facets, etc.), bone spurs (e.g., bone spurs associated with osteoarthritis), tissue of thickened ligaments, spinal tumors, displaced tissue (e.g., tissue displaced by a spinal injury), or tissue that may cause or contribute to spinal nerve compression. The instrument 110, as well as other instruments (e.g., rongeurs, debulkers, scrapers, reamers, dilators, etc.), can be used to perform one or more dilation procedures, decompression procedures, discectomies, m icrodiscectom ies, laminotomies, or combinations thereof. In procedures for treating stenosis, the instrument 110 can be used to remove tissue associated with central canal stenosis, lateral recess stenosis, and/or other types of stenosis. In some decompression procedures, the instrument 110 can be a tissue removal device used to, for example, remove bone, separate the ligamentum flavum from one or both vertebrae 440, 444, cut or debulk the ligamentum flavum, remove loose tissue, and remove at least a portion of the intervertebral disc 430. Each stage can be performed with a different instrument. Instruments can be selected to treat, without limitation, spinal nerve compression (e.g., spinal cord compression, spinal nerve root compression, or the like), spinal disc herniation, osteoporosis, stenosis, or other diseases or conditions.

The instrument 110 and the visualization device 140 can be positioned along different paths. For example, the instrument 110 can be positioned along a posterior path, whereas the visualization device 140 can be positioned along a transforaminal or oblique path. The ports 472, 474 are positioned at different superior-inferior positions, and the port 472 is positioned directly posterior to the treatment site such that a longitudinal axis of the tissue removal device 110 lies in a plane that is generally parallel to a transverse plane of the subject. The visualization device 140 can be, without limitation, an endoscopic instrument that includes fiber optics 480 suitable to image the ligamentum flavum, spinal cord, nerves branching from spinal cord, ligament, vertebrae 440, 444, intervertebral disc 430, or any other features or anatomical structures of interest while the instrument 110 removes tissue (e.g., bone from the vertebrae 440, 444 or tissue intervertebral disc 430).

Figure 5:
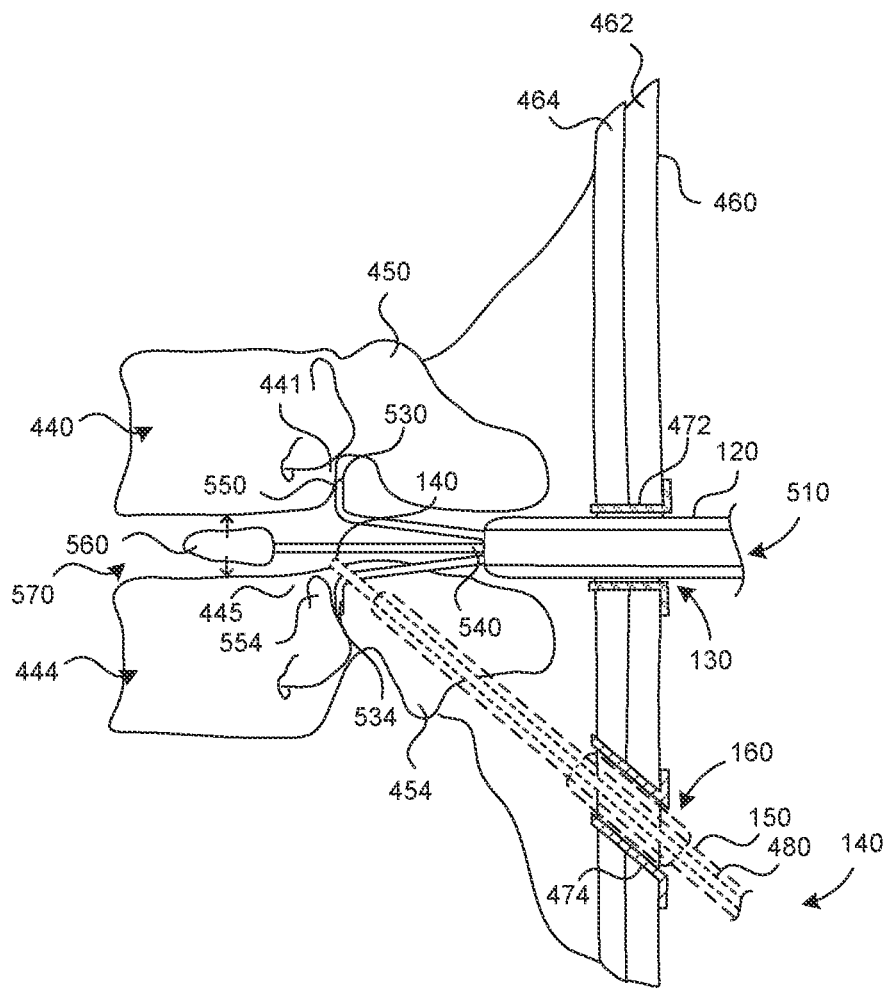
FIG. 5 is a side view of a distraction instrument with a collapsed expansion element positioned at an intervertebral space and a visualization device in accordance with an embodiment of the disclosure.

FIG. 5 is a side view of a distraction instrument with a collapsed expansion element positioned between two vertebrae after an intervertebral disc has been removed in accordance with an embodiment of the disclosure. A distraction instrument 510 is positioned in the cannula 120 and has positioners or stops 530, 534 and an expander or distractor head 560 ("expander 560"), illustrated in a partially expanded state, configured to push apart the adjacent vertebrae 440, 444. Expansion of the expander 560 and the positioners 530, 534 can be viewed endoscopically with the visualization device 140.

The positioners 530, 534 are configured to help position the expander 560 insertable into an intervertebral space 570. For example, the positioner 530 can contact an inferior vertebral notch 550 of the vertebral body 441, and the positioner 534 can contact a superior vertebral notch 554 of the vertebral body 445. An elongate member 540 can be extended or contracted to position the expander 560 at a desired location, while the positioners 530, 534 can remain relatively stationary relative to the vertebral bodies 441, 445. Throughout this process, the visualization device 140 can be used to view the positioners 530, 534, the elongate member 540, and/or the expander 560. A physician can confirm the condition of expander 560 relative to anatomical features prior, during, and after expansion. This ensures that the expander 560 contacts desired regions of the spinal column. The expander 560 can be deployed to push against endplates of the adjacent vertebrae 440, 444, thereby enlarging the intervertebral space 570.

The positioners 530, 534 can include spikes, protrusions, or other movement-inhibiting elements. In some embodiments, anchors or protrusions can be connected directly to the elongate member 540 and can be deployed to engage the endplates. The configuration, number, and position of the positioners can be selected based on the desired positioning relative to the spinal column.

The elongate member 540 is connected to the expander 560 and can be a rod with one or more lumens through which fluid flows. Fluid (e.g., saline, gas, or another suitable fluid) can be pumped through the elongate member 540 to inflate the expander 560. For fluoroscopy, the fluid can include a contrast media. The expander 560 can include, without limitation, one or more inflatable members, balloons, mechanical expanders, wedging devices, or the like. Arrows indicate one of the many possible directions of expansion, and the direction of expansion of the expander 560 is not limited to bidirectional expansion.

The distraction instrument 510 can also deliver an interbody fusion implant and serve as a driver instrument. The distraction instrument 510 can have a shaft connectable to the interbody fusion implant. The shaft can be rotated to deploy the interbody fusion implant. U.S. Pat. Nos. 8,632,594, 9,308,099, 10,105,238 and 10,201,431, which are hereby incorporated by reference and made a part of this application, disclose driver components that can be incorporated into the distraction instrument 510.

Figure 6:
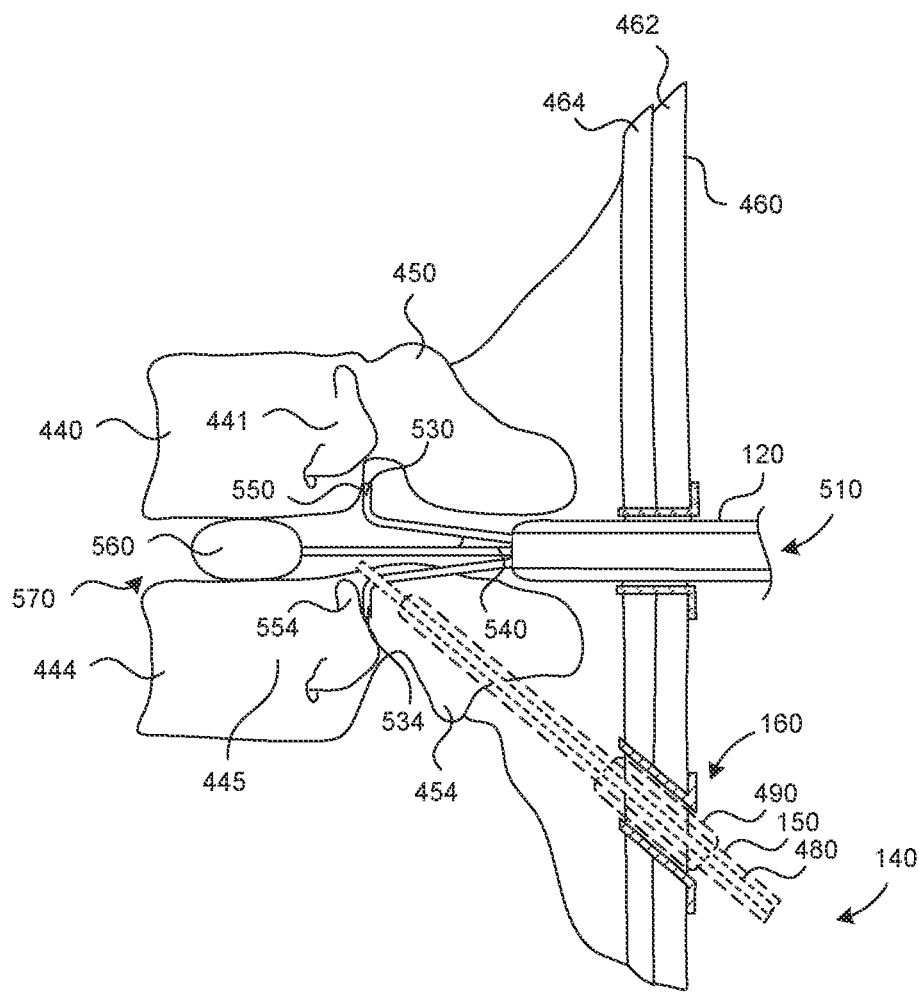
FIG. 6 is a side view of the distraction instrument with the inflated expansion element contacting endplates of vertebral bodies in accordance with an embodiment of the disclosure.

FIG. 6 is a side view of the distraction instrument 510 with an inflated expansion element 560 holding apart the vertebral bodies 441, 445. The level of expansion of expander 560 can be increased or decreased to increase or decrease, respectively, the pressure applied to the endplates. The expander 560 can include one or more roughened surfaces, spikes, protrusions, or other features capable of roughening, abrading, scraping, or otherwise affecting tissue. In some embodiments, the expander 560 has a plurality of protruding spikes that can be used to roughen the opposing vertebral endplate surfaces to help limit or substantially prevent migration of an implanted device. The expander 560 can be collapsed and removed. Another expander can be inserted into the already-expanded intervertebral space 570 to further distract the vertebrae 440, 444. In this manner, the vertebrae can be sequentially distracted in a controlled manner until a desired amount of separation is achieved.

The expander 560 can hold apart the distracted second vertebral bodies 441, 445 while an interbody fusion implant is delivered through the distraction instrument 510 and into the intervertebral space 570. The interbody fusion implant can be positioned adjacent to the deployed expander 560, which can be removed after, for example, deploying the interbody fusion implant.

The configuration of the instruments can be selected based, at least in part, on the distance from the portal sites to the treatment site. The surgical procedure can be selected based on the steps to be performed. For example, TLIF and PLIF surgery can include a decompression procedure in which tissue along the posterior region of the spine is removed in contrast to an ALIF procedure in which no such decompression procedure is performed. The systems and techniques discussed in connection with FIGS. 4-6 can be modified to perform other types of procedures, including non-spine procedures.

Figure 7:
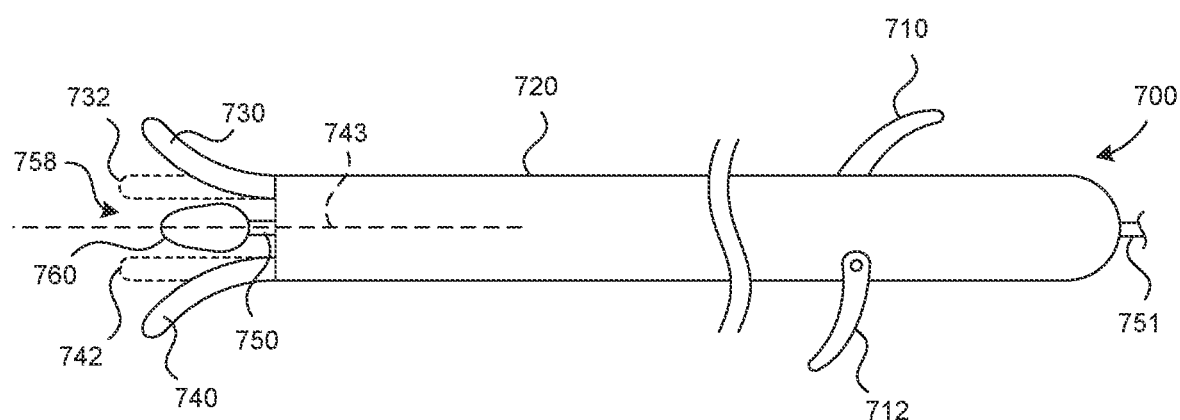
FIG. 7 is a side view of a distraction instrument with an expansion element in accordance with an embodiment of the disclosure.

FIG. 7 is a side view of a distraction instrument 700 with an expansion element in accordance with an embodiment of the disclosure. The instrument 700 can include control elements 710, 712, an elongated body 720, positioners 730, 740, and an expander assembly 758. The control elements 710, 712 can be operated to deploy the positioners 730, 740 and/or expander assembly 758. For example, a user can manually rotate the control elements 710, 712 to independently deploy the respective positioners 730, 740. For example, the control element 710 can be used to rotate the positioners 730, 740 away from undeployed positions 732, 742 (illustrated in dashed line) and a longitudinal axis 743 of the instrument 700 and toward the illustrated outwardly deployed positions.

The distraction instrument 700 can be used in a similar manner as described in connection with FIGS. 5 and 6. For example, the deployed positioners 730, 740 can rest against adjacent vertebrae. The expander assembly 758 has an expander or distractor head 760 ("expander 760") positionable at a desired location suitable for distracting the vertebrae. The expander assembly 758 can include an elongated body 750 fluidically connected to a fluid line 751. The expander 760 can be mounted to the distal end of the elongate body 750 such that fluid can be pumped through the fluid line 751, through the elongated body 750, and into the expander 760.

Figure 8:
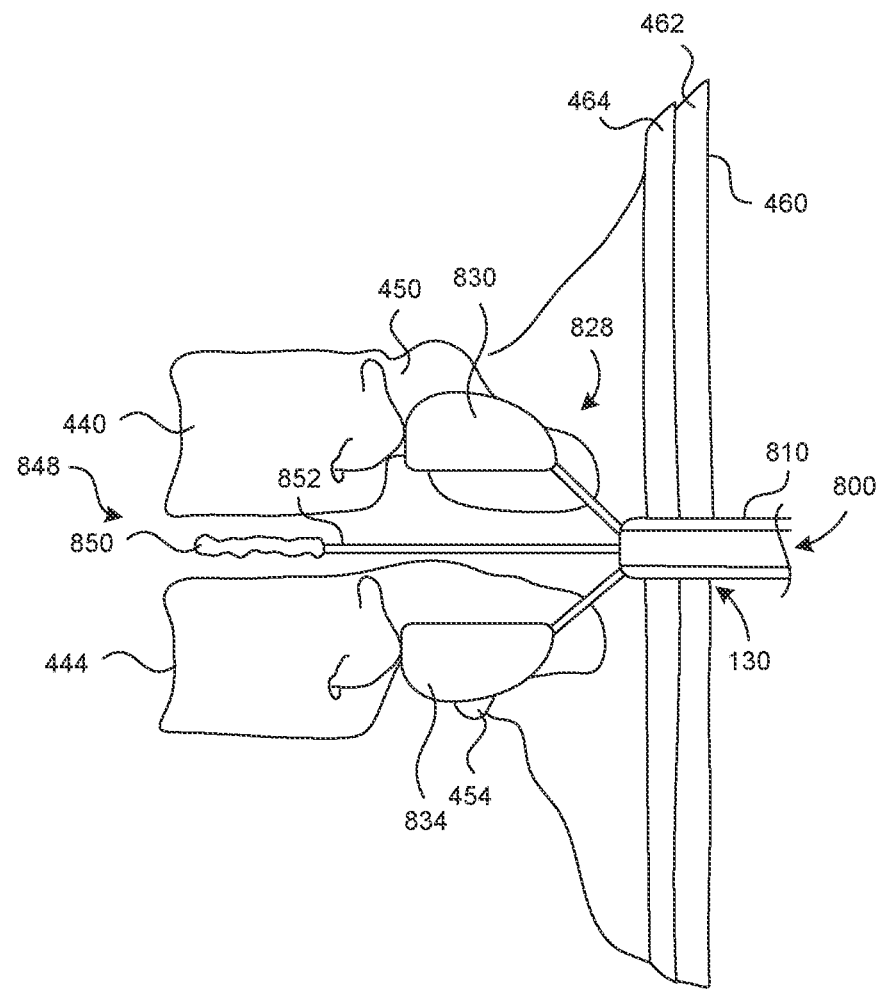
FIG. 8 is a side view of an instrument positioned between two vertebrae in accordance with an embodiment of the disclosure.

FIG. 8 is a side view of an instrument 800 positioned to distract adjacent vertebrae in accordance with an embodiment of the disclosure. A description of the instruments discussed in connection with FIGS. 4-7 applies equally to the instrument 800 unless indicated otherwise.

The instrument 800 can include an access device or cannula 810 and a distraction assembly 828. The cannula 810 can serve as an access device through which the distraction assembly 828 can be delivered. The distraction assembly 828 can include positioners 830, 834 configured for atraumatic contact with the spinal column. The positioners 830, 834 can be inflatable members (e.g., inflatable balloons), mechanically expanded members, or other types of elements. The positioners 830, 834 can be configured to contact vertebral bodies, transverse processes, spinous processes, or the like. The distraction assembly 828 can further include an expandable assembly 848 with an expander 850 and an elongated body 852. The illustrated expander 850 is in a collapsed, deflated configuration or state. The expander 850 can be expanded/inflated in a manner similar to the expander 560 discussed in connection with FIGS. 5 and 6. A visualization device can be used to view the expander 850, positioners 830, 834, or other features of the instrument before, during, and/or after the distraction process. In some embodiments, the distraction assembly 828 can function as a jaw in which the positioners 830, 834 can be used to grip or define a delivery gap. Additionally or alternatively, the positioners 830, 834 can be inserted into spaces (e.g., cavities) and then moved apart to expand the spaces.

Figure 9A:
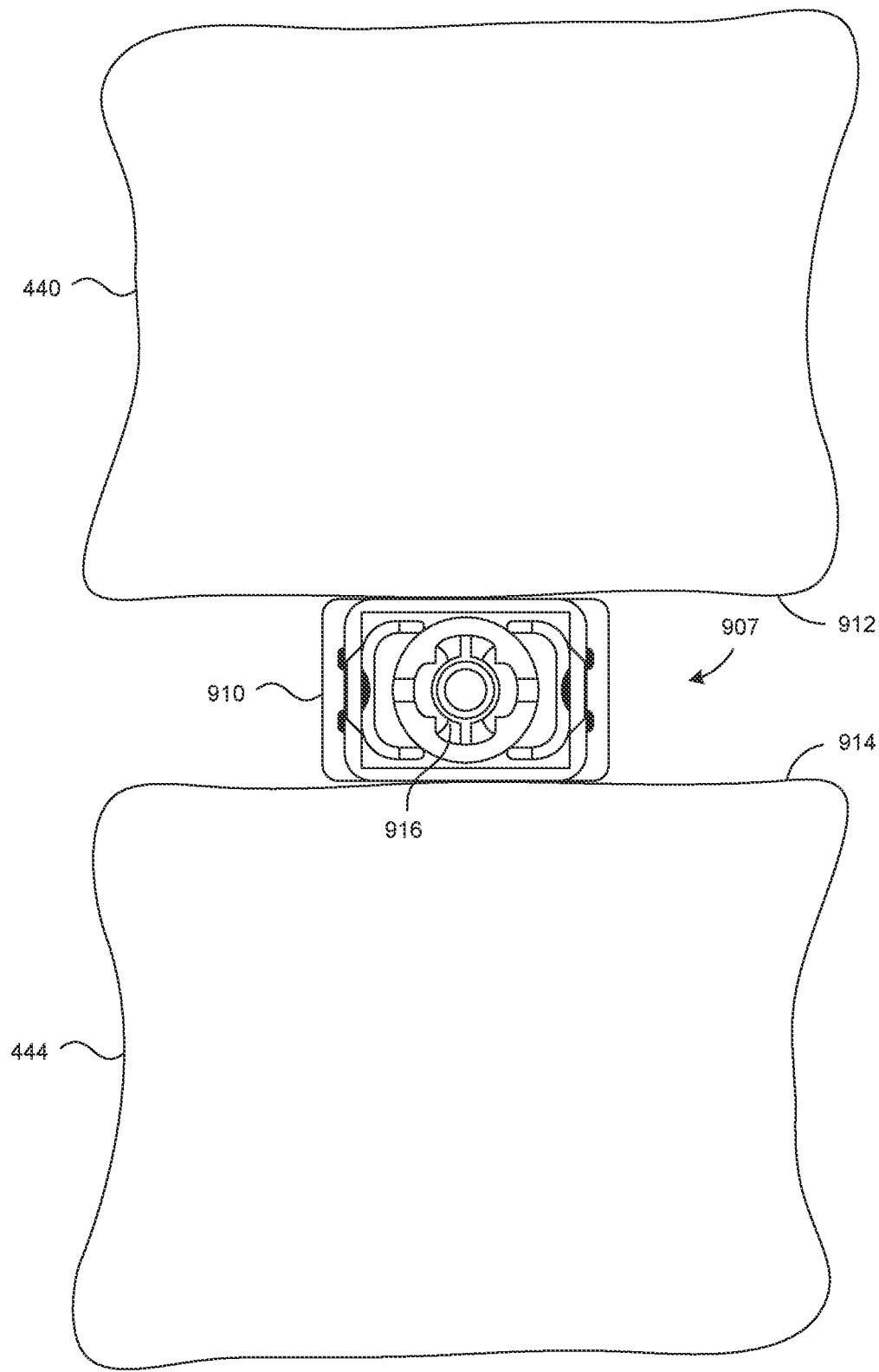
FIGS. 9A, 9B, and 9C are views from an anterior direction of a subject's spine with an interbody spacer positioned between vertebrae in accordance with an embodiment of the disclosure.
Figure 9B:
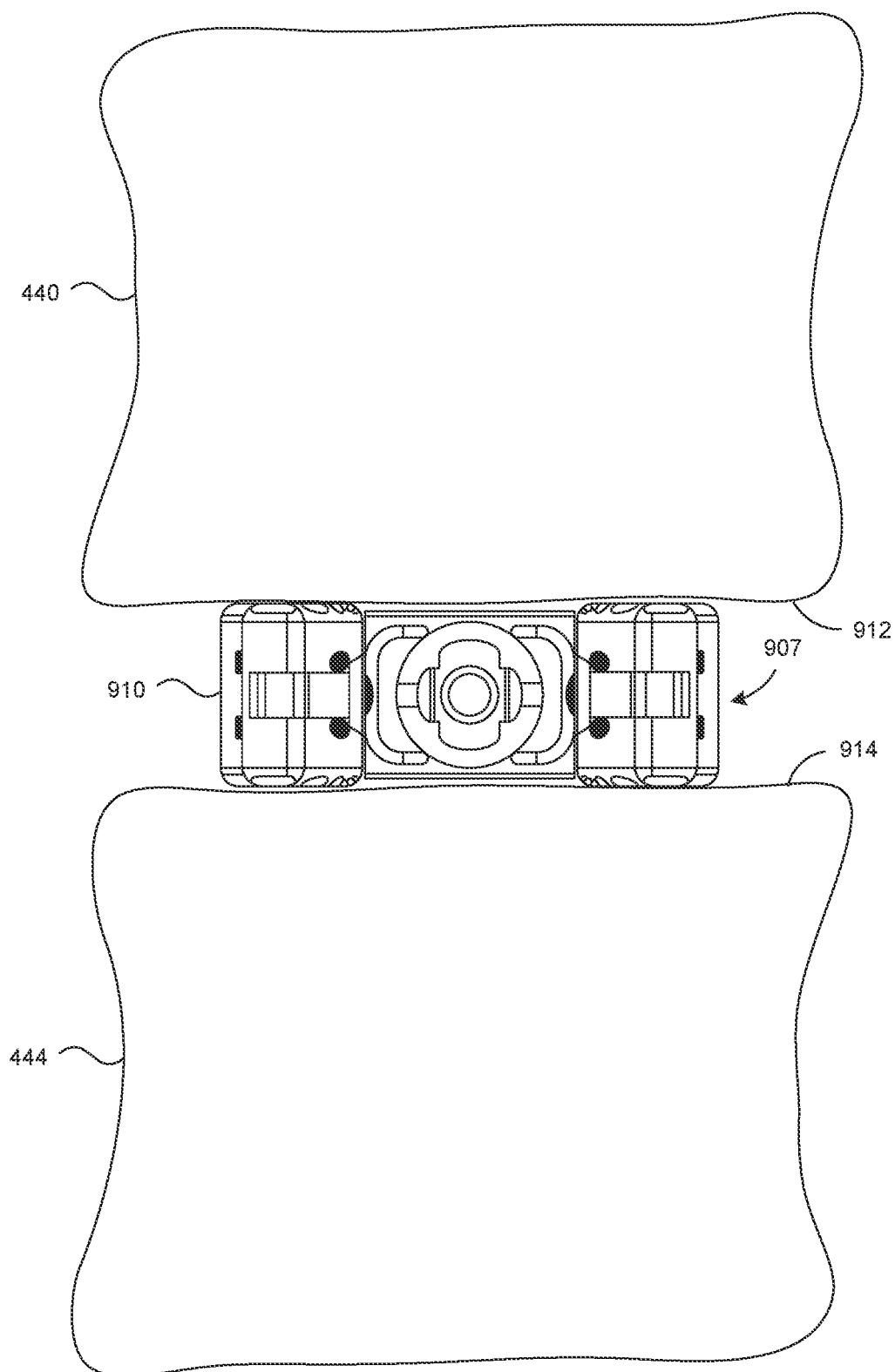
Figure 9C:
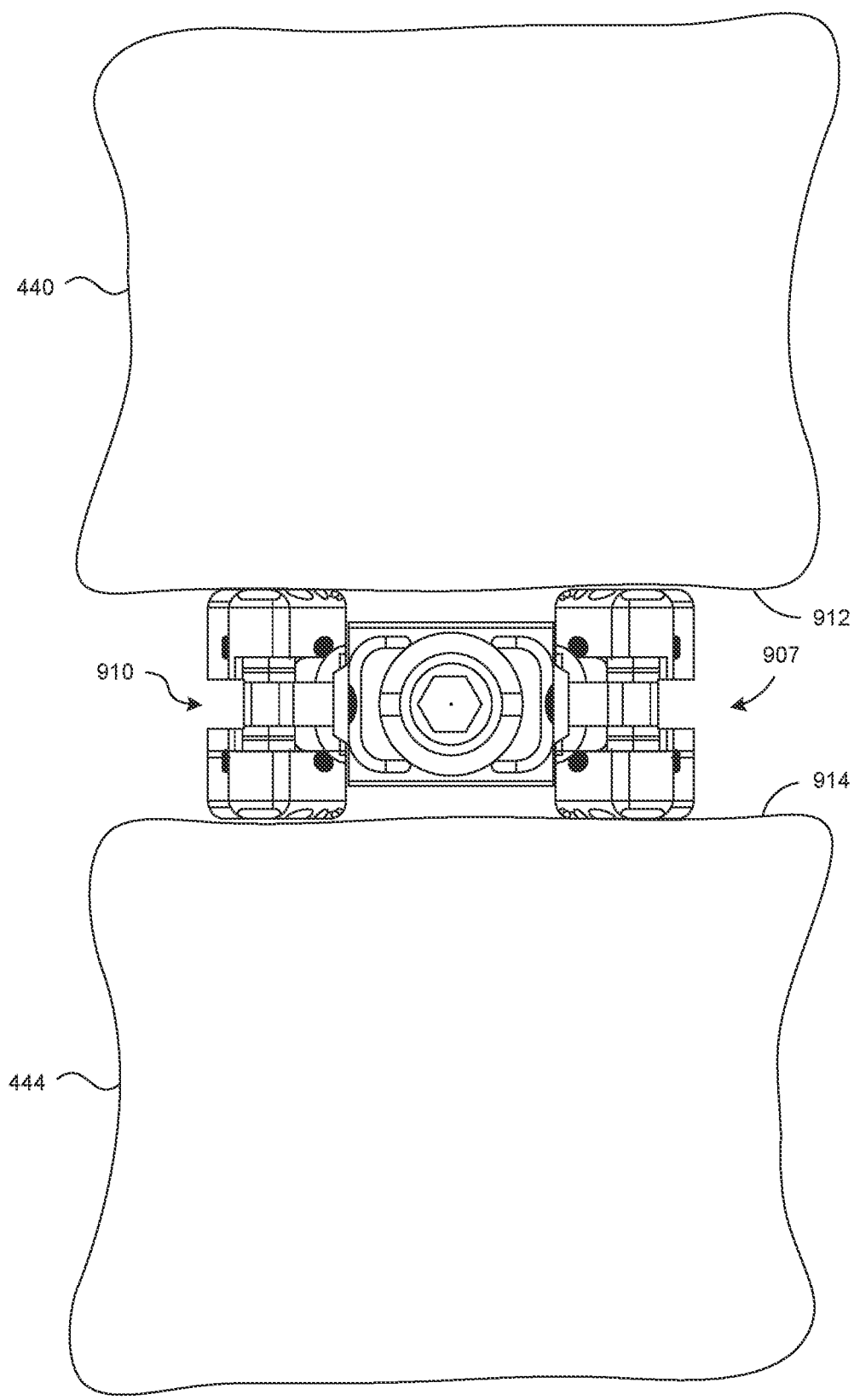

FIGS. 9A, 9B, and 9C are anterior views from an anterior direction of a subject of an interbody spacer 910 between two vertebrae in accordance with an embodiment of the disclosure. In FIG. 9B, the interbody spacer 910 is in a laterally expanded configuration. In FIG. 9C, the interbody spacer 910 is in a laterally and vertically expanded configuration. In general, the interbody spacer 910, in a collapsed configuration, can be delivered into an intervertebral space. After endoscopically viewing the position of the interbody fusion implant, the implant can be moved from the collapsed configuration (FIGS. 9A and 10A) to an expanded configuration (FIGS. 9C and 10B). The expansion (e.g., lateral expansion, vertical expansion, combinations thereof, etc.) can be viewed using the endoscopic instrument. The interbody spacer 910 can be, without limitation, an implant, an interbody fusion implant, or the like. Details of the operation of the interbody spacer 910 are discussed in detail below.

Referring now to FIG. 9A, the intervertebral disc has been removed from the intervertebral space 907. The interbody spacer 910 can be delivered through a cannula, such as the cannula 120 of FIGS. 1-7 or the cannula 810 of FIG. 8, to position the collapsed interbody spacer 910 directly between endplates 912, 914 of the vertebrae 440, 444, respectively. The position of the collapsed interbody spacer 910 can be confirmed via endoscope viewing. If the interbody spacer 910 is at an undesired position, the interbody spacer 910 can be moved to another position. Once again, endoscopic viewing can be used to confirm the final position of the interbody spacer 910.

FIG. 9B shows the interbody spacer 910 after it has been laterally expanded under endoscopic viewing. Advantageously, if the expansion process causes unwanted displacement of the interbody spacer 910, the user can reposition the interbody spacer 910.

FIG. 9C shows the interbody spacer 910 after it has been vertically expanded against endplates 912, 914 of the vertebrae 440, 444, respectively. After full expansion, the interbody spacer 910 can be locked to prevent collapse. Optional material can be delivered to the intervertebral space 907 to promote or facilitate fusion. For example, material can be delivered into the intervertebral space 907 via a delivery instrument 920 (FIG. 10A) connected to the interbody spacer 910. The material can be bone, bone-growth-inducing materials, cement, or other suitable material. The bone-growth-inducing materials can be configured to promote bony arthrodesis. In some procedures, the material is delivered through passageway of the delivery or driver instrument. In other procedures, the material can be delivered via a separate instrument. In some procedures, multiple interbody spacers are implanted at the intervertebral space 907. Details of delivery instruments are discussed in connection with FIGS. 10A and 10B.

Figure 10A:
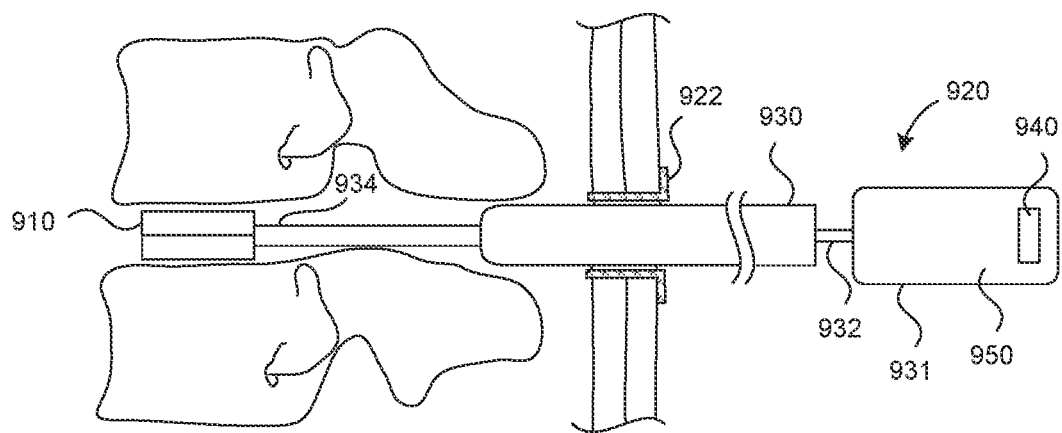
FIG. 10A is a side view of the interbody spacer in a collapsed configuration.
Figure 10B:
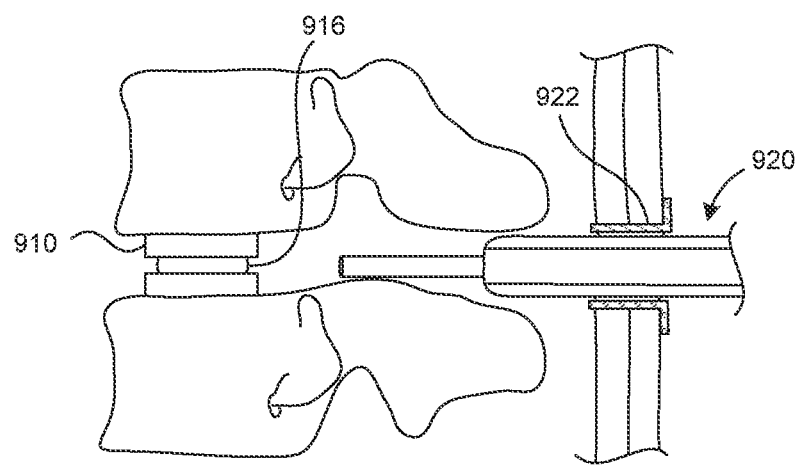
FIG. 10B is a side view of the interbody spacer in an expanded configuration.

Referring to FIG. 10A, the interbody spacer 910 and delivery instrument 920 can be delivered through a port 922, with or without the use of a cannula 930. The instrument 920 can include a handle assembly 931, an elongated body 932, and a connecter 934. The handle assembly 931 can include a grip 950 and one or more control elements 940 operable to control operation of the interbody spacer 910 and control decoupling from the interbody spacer 910. In some embodiments, the control elements 940 can include one or more dials, levers, triggers, or other movable elements. The elongated body 932 is connected to the handle 950 and extends to the connecter 934. The elongated body 932 can serve as a driver instrument and can include one or more rods, shafts, or other elements used to operate the interbody spacer 910. In some embodiments, a driver instrument is inserted through the delivery instrument 920 and into engagement with the interbody spacer 910. The driver instrument can be rotated to gradually and controllably deploy the interbody spacer 910. The features, configuration, and functionality of the connector 934 can be selected based on the configuration of the interbody spacer 910.

FIG. 10B is a side view of the of the expanded interbody spacer 910 after the delivery instrument 920 has been separated from a connection feature or connection interface 916 ("connection feature 916") of the interbody spacer 910. The expanded interbody spacer 910 can be locked in the expanded configuration. To reposition the interbody spacer 910, the delivery instrument 920 can be reconnected to the interbody spacer 910 and operated to unlock and collapse the interbody spacer 910. The delivery instrument 920 can be used to move the collapsed interbody spacer 910.

The delivery instrument 920 can include one or more distal connection elements or features for detachably coupling to the interbody spacers. The connection elements can be a polygonal connection (e.g., a hexagonal protrusion) received by a complementary polygonal recess or feature of the interbody spacer 910. Other connections can be used to detachably couple the delivery instrument 920 to the interbody spacer 910. U.S. Pat. Nos. 8,632,594, 9,308,099, 10,105,238 and 10,201,431, which are hereby incorporated by reference, disclose delivery instruments, interbody spacers, connection features, and methods of operating delivery instruments and deploying interbody spacers. The delivery instrument 920 can be a delivery instrument and include features disclosed in U.S. Pat. Nos. 8,632,594, 9,308,099, 10,105,238 and 10,201,431. Other types of implantable devices and delivery instruments can be utilized. The configuration of the implant and corresponding delivery instruments can be selected based on the procedure to be performed.

Figure 11:
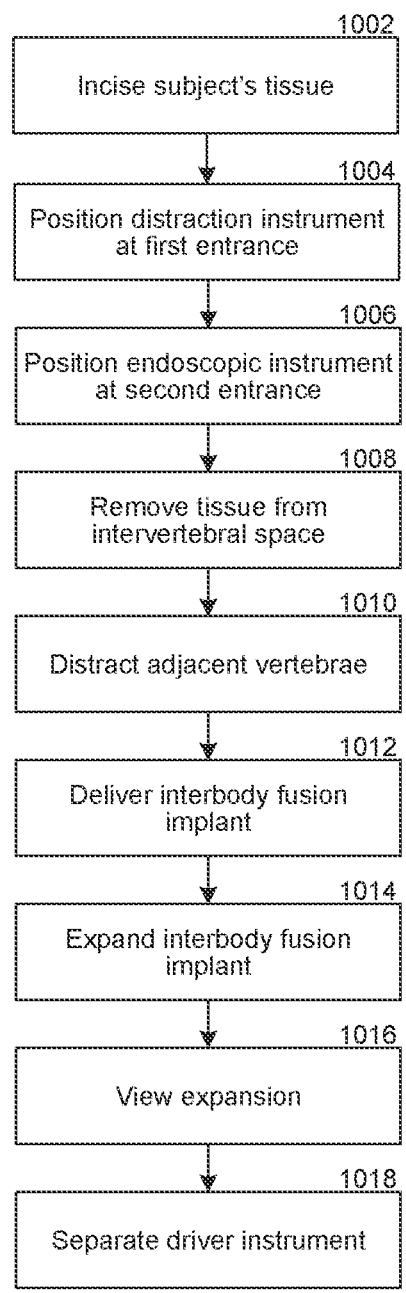
FIG. 11 is a flow diagram illustrating a method for performing a spine surgery in accordance with an embodiment of the disclosure.

FIG. 11 is a flow diagram illustrating a method for treating a subject in accordance with an embodiment of the disclosure. In block 1002, incisions can be made in the subject's tissue to create first and second portal sites (i.e., entrances). In some embodiments, the first and second entrances can be positioned on the same side of the subject's midsagittal plane. In other embodiments, the first and second entrances can be positioned on opposite sides of the subject's midsagittal plane. In yet other embodiments, the incisions can be made along the subject's midsagittal plane.

Ports can be installed in each of the entrances. The sizes of the ports can be selected based on the size of the incision and characteristics of the tissue at the port site. For example, a tubular body of the port can be sufficiently long to extend through the subject's skin, fascia, and muscle. An access opening of the port can be sufficiently large to allow instruments to be inserted into and through the ports, which can prevent or inhibit tearing of tissue. Instruments can be delivered through the incisions into the patient without utilizing ports. Such instruments can have relatively small diameters to limit or inhibit tearing of the tissue around the incision. In some procedures, ports can be installed in some incisions and instruments can be installed in other incisions without ports. A physician can determine whether to install ports based on the instruments to be utilized and the position of the incisions.

In block 1004, a distraction instrument can be positioned at the first portal site by inserting the distraction instrument through, for example, an installed port. In some procedures, a cannula can be positioned in the port and the distraction instrument can be delivered through the lumen of the cannula. In other embodiments, the distraction instrument can be inserted directly into the port without utilizing the cannula. Utilization of distraction instruments and cannulas are discussed in connection with FIGS. 5-8.

In block 1006, a visualization device can be positioned at a second portal site by delivering the visualization device through a port. The visualization device can be installed with or without use of the cannula. Utilization of a cannula and a port are discussed in connection with FIGS. 1-7. In some embodiments, the visualization device can be a low-profile fiber optic visualization system deliverable through a portal site in the form of a small incision. In these procedures, a cannula may not be used since the visualization device has a small diameter. The visualization device can be kept at the same portal site throughout most of the surgical procedure period in which the spine is altered. For example, the visualization device can be positioned at a single portal site for at least 80% or 90% of the surgical period in which instruments are positioned in the subject. The visualization device can be positioned within the subject such that an interbody fusion device is capable of being implanted without removing the endoscope from the subject. This can reduce the overall surgery time.

A steerable visualization device can be used to facilitate navigation around anatomical features. The steerable visualization device can include a fiberoptic scope, or a flexible or rigid instrument with one or more illumination elements (e.g., fiber-optics for illumination) or imaging elements (e.g., charge-coupled devices for imaging) suitable for visualizing the interior of otherwise inaccessible sites. In some embodiments, the visualization device can be rod-lens endoscopes with an outer diameter equal to or smaller than about 2 mm, 3 mm, 4 mm, 5 mm, 6 mm, 8 mm, or 10 mm; and a length equal to or shorter than about 15 cm, 20 cm, 30 cm, or 40 cm. The device can also have connectors (e.g., electrical connectors, fluidic connectors, etc.), access ports (e.g., access ports connected to lumens (e.g., lumens through which instruments can pass)), or the like. In embodiments with an angled lens, the visualization instrument can have approximately 15 degree, 30 degree, or 45 degree lens angles, which are toward a light source. In other angled lens embodiments, the visualization instrument can have an approximately 15 degree, 30 degree, or 45 degree lens angled away from a light source. The angle of the lens can be selected based on the area to be viewed. In some posterior or lateral spinal procedures, a 0 degree lens can provide a wide-angle view suitable for viewing nerve roots, the spinal cord, and intervertebral space. A 30 or 45 degree lens endoscope angled toward the light source can be used to provide an angled view toward, for example, the midsagittal plane to view, for example, the spinous processes, spinal cord, central regions of the intervertebral space. A 30 or 45 degree lens endoscope angled away from the light source can be used to provide an angled view toward the lateral features or the spine, such as nerve roots at the neural foramen, side regions of the intervertebral space, or the like.

In some procedures, multiple visualization instruments are utilized. In one procedure, multiple visualization instruments are positioned within the same port, which is large enough to allow relative movement between the endoscopic instruments. In other procedures, endoscopic instruments are positioned in spaced apart ports. To provide bilateral viewing, a first port and first endoscopic instrument can be positioned on one side of the midsagittal plane of the subject, and the other port and endoscopic instrument can be positioned on the other side of the midsagittal plane. Multiple visualization instruments used in a single procedure can have different viewing characteristics.

The images of the subject's spine can be used to determine implantation information about the interbody fusion implant. Implantation information can include, without limitation, a recommended interbody fusion implant, expansion setting for the interbody fusion implant, and/or recommended implantation position for the interbody fusion implant. The user can be presented information for viewing based on the analysis of the image data, including information for repositioning the interbody fusion implant or information for collapsing the interbody fusion implant. In block 1008, tissue from the intervertebral space can be removed with a tissue removal device positioned at the first entrance. In block 1010, adjacent vertebrae can be distracted using the distraction instrument to enlarge the intervertebral space between the adjacent vertebrae. In block 1012, an interbody spacer, such as an interbody fusion implant, can be delivered to the enlarged intervertebral space. The interbody fusion implant can be delivered in a collapsed configuration through a lumen of the distraction instrument. In block 1014, the interbody fusion implant can be expanded laterally and vertically while a driver instrument is positioned within the distraction instrument positioned at the first entrance and while being endoscopically viewed in block 1016. The lateral and vertical expansion of the interbody fusion implant can be sequential. For example, after the interbody fusion implant is horizontally expanded, the interbody fusion implant can be vertically expanded to provide disc height restoration.

In block 1016, image data can be obtained by an endoscopic instrument. The image data can be video, still images, or other image data. Image data can be obtained before, during, and/or after expansion and analyzed with endoscopic visualization to confirm the position of the expanded interbody fusion implant to improve efficacy of surgeries by allowing the physician to visually assess the procedure. For example, a first image of an implantation site can be obtained by the endoscopic instrument. A second image of the implantation site can be obtained using the endoscopic instrument after delivery of the interbody fusion implant. Image data can be analyzed to determine whether the expanded interbody fusion implant is located at a deployment position based on a position of the expanded interbody fusion implant shown in the second image.

In some embodiments, the first image and the second image can be compared to determine the position of the expanded interbody fusion implant. If the interbody fusion implant is mispositioned, the user can be notified of the mispositioning. The notification can be via an audible alert, visual alert (e.g., an alert displayed on the display 162 at FIG. 1), or by other suitable notification means. In block 1018, the driver instrument can be separated from a locked expanded interbody fusion implant, as discussed in connection with FIG. 10B. The implanted interbody fusion implant can be visualized to confirm proper positioning and deployment of the implant. Visualization can be used if additional procedures are performed. Additional procedures may include, without limitation, delivering bone, growth-promoting materials, or the like to the intervertebral space. Visualization can also be used to view other procedures, such as fixation procedures involving pedicle screws, interspinous spacers, or the like.

The method of FIG. 11 can be performed using various systems disclosed herein. Additional instruments and steps can be performed as needed to provide treatment flexibility. For example, decompression procedures can be performed before or after distracting the adjacent vertebrae at block 1010. Visualization can be used during the decompression procedure to visually identify targeted tissue, as well as ensuring that non-targeted tissue (e.g., nerve tissue) is not traumatized. Although the method is discussed in connection with implanting an interbody fusion implant, the method can be performed to deploy and implant other devices. For example, the method can be used to implant an articulating intervertebral disc. Moreover, the multi-portal systems can be used to implant rigid or fixed interbody fusion devices. The acts and steps in the method of FIG. 11 can be modified based on the features of the implant to perform, for example, an oblique lumbar interbody fusion procedure, a lateral lumbar interbody fusion procedure, a posterior lumbar interbody fusion procedure, a transforaminal lumbar interbody fusion procedure, or an anterior lumbar interbody fusion procedure.

Figure 12:
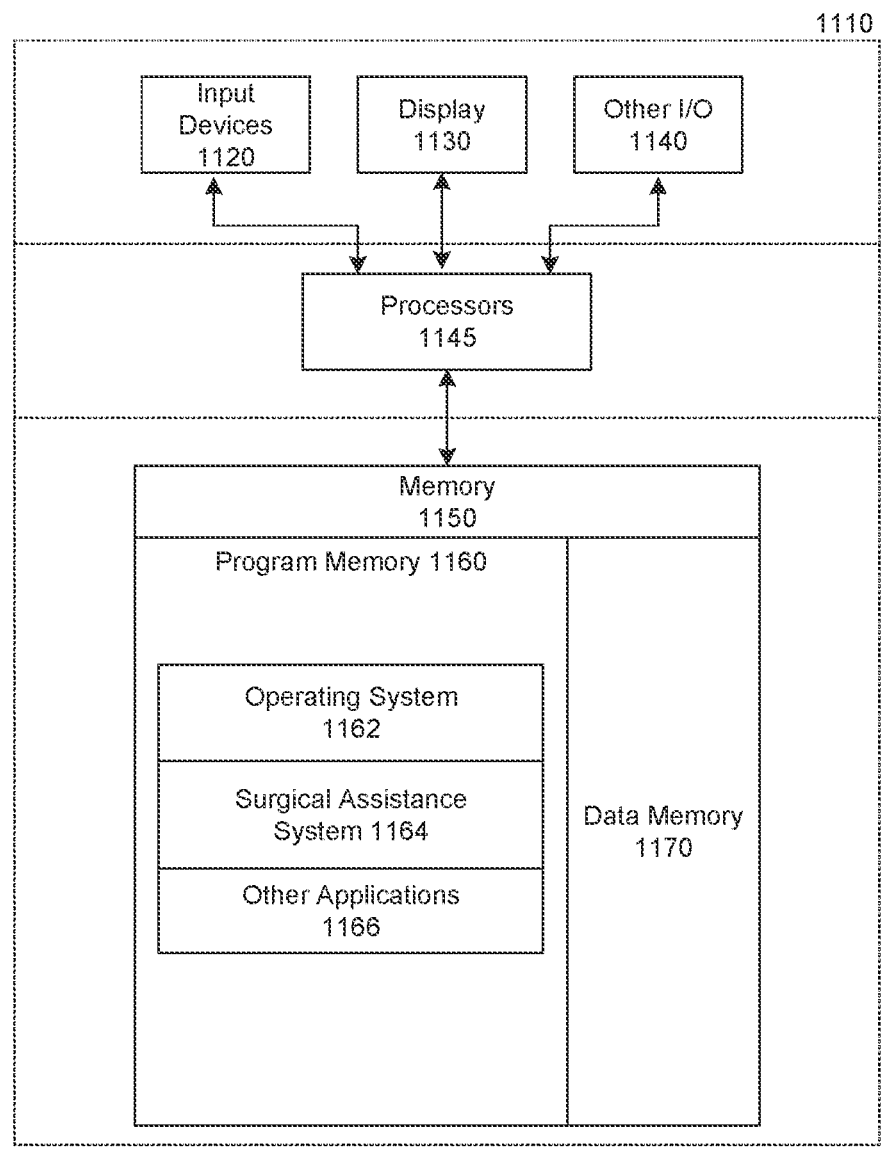
FIG. 12 illustrates a system for providing assistance prior to, during, or after surgery according to an embodiment of the disclosure.

FIG. 12 illustrates a system 1110 for providing surgical assistance according to an embodiment of the disclosure. The system 1110 can improve surgeries by displaying image data, analyzing image data, suggesting steps in a surgical procedure, analyzing implants, or the like. The system 1110 can comprise hardware components that improve surgeries using, for example, a surgical assistance system 1164. In various implementations, the surgical assistance system 1164 can store patient information, obtain image data, analyze information/data to obtain results, and use the results to provide feedback to a user. The surgical assistance system 1164 can analyze still images or video from input devices 1120 to suggested implants for a procedure. For example, the surgical assistance system 1164 can recommend the number, size, and configuration of implants and surgical procedure. Based on the recommendations, the surgical assistance system 1164 can further suggest surgical instruments, a surgical plan, and other information. The surgical plan can include (1) surgical steps, (2) number, size, and/or position of ports, and/or (3) surgical approaches. For example, the surgical assistance system 1164 can annotate an image (e.g., an X-ray image, still image, video, etc.) with suggested insertion points along the subject's skin, surgical procedures (e.g., PLIF, ALIF, LLIF, etc.), access paths, etc. During a procedure, the surgical assistance system 1164 can provide warnings or other feedback to surgeons.

System 1110 can include one or more input devices 1120 that provide input to the processor(s) 1145 (e.g., CPU(s), GPU(s), HPU(s), etc.), notifying it of actions. The actions can be mediated by a hardware controller that interprets the signals received from the input device and communicates the information to the processors 1145 using a communication protocol. The processors 1145 can be used to analyze data, such as image data, to determine whether the expanded interbody fusion implant is located at a deployment position based on a position of the expanded interbody fusion implant shown in an acquired image.

Input devices 1120 can include, for example, visualization devices, such as the visualization device 140 discussed in connection with FIGS. 1-6, endoscopic instruments, imaging devices (e.g., cameras), CRT machines, X-ray machines, or the like. The visualization, in some surgical embodiments, enables surgeons to visually see and verify the vertebral bodies, vertebral spacing, damaged/displaced tissue, intervertebral discs (including bulging portions), presence of unwanted cartilage (e.g., cartilage buildup), bone, or tissue that is causing nerve root compression and damage to normal body functions. This information on the unwanted material can be documented and recorded by saving image data into a computer database and printing color images (e.g., pictures) immediately for reference and recording. The physician can use the information to develop at least a portion of a surgical plan.

Additionally or alternatively, the input devices 1120 can include a mouse, a keyboard, a touchscreen, an infrared sensor, a touchpad, a wearable input device, a camera- or image-based input device, a microphone, or other user input devices. For example, a mouse can be used to select or manipulate image data captured by visualization devices. A keyboard can be used to annotate image data. The number and configuration of the input devices can be selected based on the physician.

Processors 1145 can be a single processing unit or multiple processing units in a device or distributed across multiple devices. Processors 1145 can be coupled to other hardware devices, for example, with the use of a bus, such as a PCI bus or SCSI bus. The processors 1145 can communicate with a hardware controller for devices, such as for a display 1130. The display 1130 can be used to display image data. For example, the display 1130 can correspond to the display 162 in FIG. 1, which can be connected to one or more visualization devices via a wired or wireless connection (FIG. 1 shows a wired connection). The display 1130 can present information for viewing by a user. The presented information can include suggested implant information, suggested surgical instruments, information for implanting devices, information for repositioning the interbody fusion implant, information for collapsing the interbody fusion implant, or the like. The information can be overlaid on or inserted into images or video. In some embodiments, the information can be annotations.

The display 1130 can provide graphical and textual visual feedback to a user. In some implementations, the display 1130 includes the input device as part of the display, such as when the input device is a touchscreen or is equipped with an eye direction monitoring system. In some implementations, the display is separate from the input device. Examples of display devices are: an LCD display screen, a light-emitting diode (LED) display screen, a projected, holographic, or augmented reality display (such as a heads-up display device or a head-mounted device), and so on. The display 1130 can provide high definition visualization.

Other I/O devices 1140 can also be coupled to the processor, such as a network card, video card, audio card, USB, firewire or other external device, camera, printer, speakers, CD-ROM drive, DVD drive, disk drive, or Blu-Ray device. Other I/O 1140 can also include input ports for information from directly connected medical equipment such as MRI machines, X-Ray machines, etc. Other I/O 1140 can further include input ports for receiving data from these types of machine from other sources, such as across a network or from previously captured data, e.g. stored in a database.

The system 1110 can also include a communication device capable of communicating wirelessly or wire-based with a network node. The communication device can communicate with another device or a server through a network using, for example, TCP/IP protocols. The system 1110 can utilize the communication device to distribute operations across multiple network devices.

The processors 1145 can have access to a memory 1150 in a device or distributed across multiple devices. A memory includes one or more of various hardware devices for volatile and non-volatile storage, and can include both read-only and writable memory. For example, a memory can comprise random access memory (RAM), various caches, CPU registers, read-only memory (ROM), and writable non-volatile memory, such as flash memory, hard drives, floppy disks, CDs, DVDs, magnetic storage devices, tape drives, device buffers, and so forth. A memory is not a propagating signal divorced from underlying hardware; a memory is thus non-transitory. Memory 1150 can include program memory 1160 that stores programs and software, such as an operating system 1162, surgical assistance system 1164, and other application programs 1166. Memory 1150 can also include data memory 1170 that can include, e.g., implantation site information (e.g., level information, implant deployment information, etc.), surgical plan data, user options or preferences, image data, etc., which can be provided to the program memory 1160 or any element of the system 1110.

Some implementations can be operational with numerous other computing systems, environments or configurations. Examples of computing systems, environments, and/or configurations that may be suitable for use with the technology include, but are not limited to, personal computers, server computers, handheld or laptop devices, cellular telephones, wearable electronics, tablet devices, multiprocessor systems, microprocessor-based systems, programmable consumer electronics, network PCs, minicomputers, mainframe computers, distributed computing environments that include any of the above systems or devices, or the like.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one skilled in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disc, a hard disk drive, a CD, a DVD, a digital tape, a computer memory, etc.; and a transmission type medium such as a digital and/or an analog communication medium (e.g., a fiber optic cable, a waveguide, a wired communications link, a wireless communication link, etc.).

C. Surgical Kits

Figure 13:
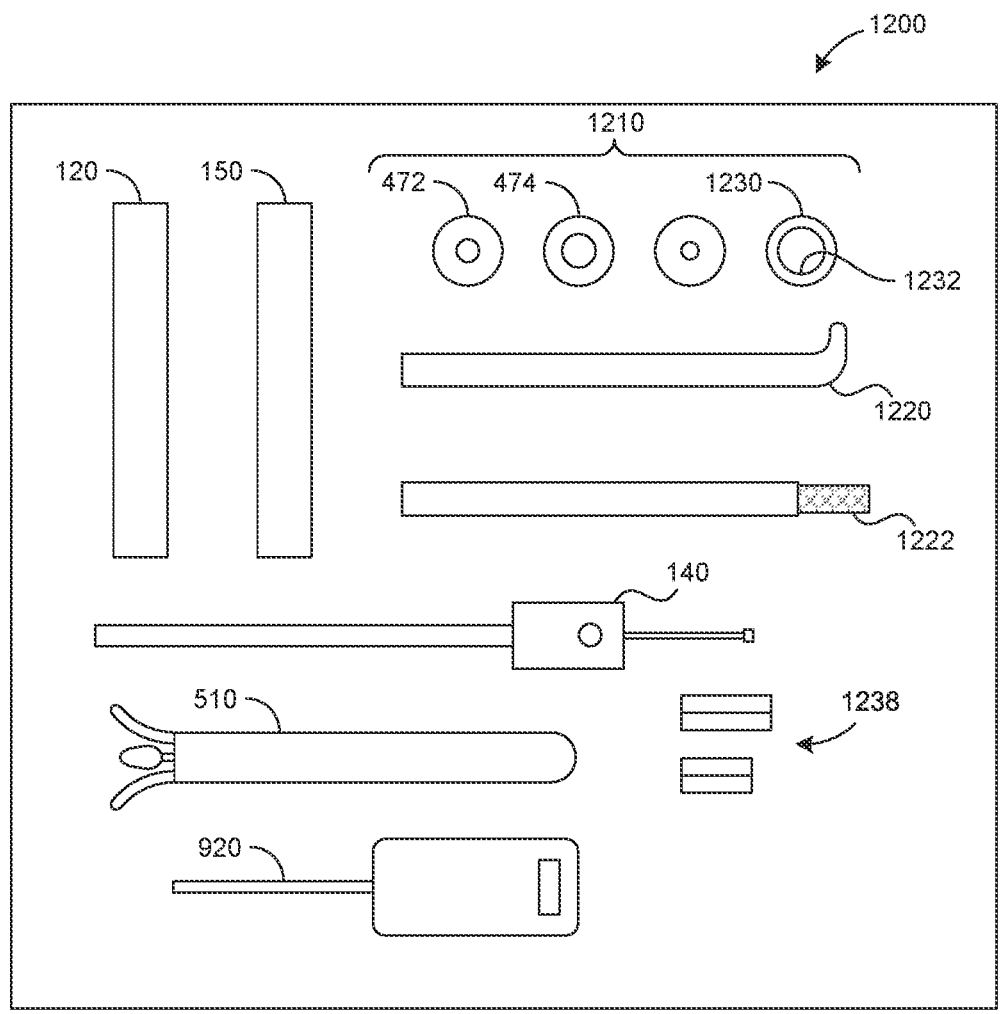
FIG. 13 is a plan view of a surgical kit in accordance with an embodiment of the disclosure.

FIG. 13 is a top plan view of a surgical kit 1200 that includes components discussed in connection with FIGS. 1-11. The kit can include cannulas 120, 150 and a set 1210 of ports. A physician can select appropriate ports based on locations of portal sites and instruments to be utilized. In the illustrative embodiment, the set 1210 includes four ports. A higher or lower number of ports can be provided and can be of the same or different sizes. The kit 1200 can include a connector (e.g., a rigid connector) to couple together cannulas (e.g., cannulas 120, 150). The cannulas can be coupled together before expanding the interbody fusion device at an intervertebral implantation site.

The kit 1200 can further include a plurality of decompression instruments. In the illustrated embodiment, the kit 1200 includes a debulking instrument 1220 and a reamer 1222. If the decompression instruments are utilized, a physician can select the port 1230 with a large opening 1232. The kit 1200 can also include scalpels, dilators, rongeurs, or other surgical instruments. The kit 1200 can include the visualization device 140, the distraction instrument 510, the delivery or deployment instrument 920, and implantable devices 1238. The configuration and components for the kit can be selected based upon the procedure to be performed. Moreover, one or more of the kit's components can be disposable and can be made from metal, polymer, ceramic, composite, or other biocompatible and sterilizable material.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. Features from various systems, methods, and instruments can be combined with features disclosed in U.S. Pat. Nos. 8,632,594, 9,308,099, 10,105,238 and 10,201,431, which are hereby incorporated by reference and made a part of this application. Variations of the implants are contemplated. For example, the interbody spacer 910 (FIGS. 9A-9C) may be provided with different overall heights covering a range of intervertebral disc heights. In other examples, the interbody spacer 910 may be provided with different lordotic and/or kyphotic angles. In still other examples, the interbody spacer 910 may be provided with other patterns or features, such as spikes, protrusions, or the like on the bone contacting surfaces that provide stability and/or resistance to shifting positions. The implant may be made from metal, polymer, ceramic, composite, or other biocompatible and sterilizable material. Different materials may be combined in what is described herein as a single part.

Systems, components, and instruments disclosed herein can be disposable or reusable. For example, the ports, instruments, or cannulas can be disposable to prevent cross-contamination. As used herein, the term "disposable" when applied to a system or component (or combination of components), such as an instrument, a tool, or a distal tip or a head, is a broad term and generally means, without limitation, that the system or component in question is used a finite number of times and is then discarded. Some disposable components are used only once and are then discarded. In other embodiments, the components and instruments are non-disposable and can be used any number of times. In some kits, all of the components can be disposable to prevent cross-contamination. In some other kits, components (e.g., all or some of the components) can be reusable.

Where the context permits, singular or plural terms may also include the plural or singular term, respectively. Moreover, unless the word 'or' is expressly limited to mean only a single item exclusive from the other items in reference to a list of two or more items, then the use of 'or' in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the present technology. Accordingly, the disclosure and associated technology can encompass other embodiments not expressly shown or described herein.

What is claimed is:

1. A multi-portal surgical method comprising:
   positioning an instrument cannula at a first entrance along a subject;
   positioning a visualization cannula at a second entrance along the subject, wherein the first and second entrances are positioned on one side of a midsagittal plane of the subject and spaced apart from one another;
   removing tissue from a working region inside the subject using at least one instrument positioned in the instrument cannula;
   endoscopically viewing the at least one instrument removing the tissue using an endoscopic viewing instrument positioned in the visualization cannula and spaced apart from the subject's spine to endoscopically view the at least one instrument removing tissue from an intervertebral space between a first vertebral body and a second vertebral body while the endoscopic viewing instrument is positioned outside of the intervertebral space to view nerve tissue adjacent the intervertebral space; and
   after removing the tissue from the intervertebral space, endoscopically viewing a first endplate of the first vertebral body and a second endplate of the second vertebral body, and
   endoscopically viewing an interbody spacer that has been delivered into the intervertebral space to view a position of the interbody spacer relative to the first and second vertebral bodies.

2. The multi-portal surgical method of claim 1, further comprising:
   using the at least one instrument to remove at least a portion of a facet and surrounding tissue of the subject to define a transforaminal path to the intervertebral space; and
   delivering the interbody spacer along the transforaminal path and into the intervertebral space.

3. The multi-portal surgical method of claim 2, further comprising endoscopically viewing, using the endoscopic viewing instrument, removal of the portion of the facet and the surrounding tissue and delivery of the interbody spacer into the intervertebral space.

4. The multi-portal surgical method of claim 2, further comprising:
   positioning the endoscopic viewing instrument to view non-targeted tissue at or near the working region; and
   removing the tissue from the working region while viewing and leaving the non-targeted tissue intact.

5. The multi-portal surgical method of claim 1, further comprising endoscopically viewing, using the endoscopic viewing instrument, nerve tissue while the tissue is being removed to avoid removal of the nerve tissue.

6. The multi-portal surgical method of claim 1, further comprising:
   viewing, using fluoroscopy, nerve compression along the subject's spine; and
   viewing, using the endoscopic viewing instrument, reduction of the nerve compression attributable to the tissue removal.

7. The multi-portal surgical method of claim 1, further comprising pumping liquid through the endoscopic viewing instrument such that the liquid carries the tissue removed from the working region out of the subject.

8. The multi-portal surgical method of claim 1,
   wherein the at least one instrument includes one or more of:
   a rongeur,
   a reamer,
   a debulker, or
   a scaper.

9. The multi-portal surgical method of claim 1, further comprising performing, under endoscopic viewing of the endoscopic viewing instrument, at least one of:
   a decompression procedure,
   a discectomy,
   a microdiscectomy, or
   a laminotomy.

10. The multi-portal surgical method of claim 1, further comprising imaging the working region using fluoroscopy while the at least one instrument and the endoscopic viewing instrument are positioned in the subject.

11. The multi-portal surgical method of claim 1, further comprising performing imaging-guided implantation by imaging, using fluoroscopy, an implant and the working region.

12. A multi-portal method for treating a subject, comprising:
    positioning an endoscopic instrument at a visualization entrance along the subject;

endoscopically viewing vertebral endplates adjacent to one another using the endoscopic instrument to determine that the vertebral endplates are prepared for contacting an implant;

distracting the adjacent vertebral endplates using a distraction instrument to enlarge an intervertebral space, wherein the distraction instrument is positioned at an instrument entrance located along the subject and spaced apart from the visualization entrance;

after determining that the adjacent vertebral endplates are prepared and distracted, moving an implant at least partially into the enlarged intervertebral space; and endoscopically viewing the implant using the endoscopic instrument, which is spaced apart from the intervertebral space, to simultaneously view the implant, the adjacent vertebral endplates, and nerve tissue proximate to the intervertebral space.

13. The multi-portal method of claim 12, further comprising using fluoroscopy to view:

the implant prior to releasing the implant from a delivery instrument, the implant during expansion of the implant in the subject, and the implant after completing expansion of the implant.

14. The multi-portal method of claim 12, further comprising endoscopically viewing, using the endoscopic instrument, one or more nerve roots and opposing side regions of the intervertebral space.

15. A multi-portal method for treating a subject, comprising:

positioning an endoscopic visualization instrument at a first entrance along the subject;

endoscopically viewing, using the endoscopic visualization instrument at the first entrance, a decompression procedure including removal of tissue along the subject's spine using a series of instruments delivered through a second entrance along the subject; and endoscopically viewing, using the endoscopic visualization instrument at the first entrance, at least one of expansion of an expansion element of an expansion instrument while viewing contact between tissue and the expansion element and nerve tissue near the expansion element; or expansion of an implant connected to a delivery instrument while viewing anatomical features and nerve tissue near the implant.

16. The multi-portal method of claim 15, wherein the expansion element is a distractor that pushes apart adjacent vertebral bodies to enlarge an interverbal space between the adjacent vertebral bodies.

* * * * *